(12) United States Patent
Gannoe et al.

(10) Patent No.: US 7,229,428 B2
(45) Date of Patent: Jun. 12, 2007

(54) METHOD AND DEVICE FOR USE IN ENDOSCOPIC ORGAN PROCEDURES

(75) Inventors: Jamy Gannoe, Redwood City, CA (US); Craig Gerbi, Mountain View, CA (US); Gary Weller, Los Gatos, CA (US)

(73) Assignee: Satiety, Inc., Palo Alto, CA (US)

( * ) Notice: Subject to any disclaimer, the term of this patent is extended or adjusted under 35 U.S.C. 154(b) by 155 days.

(21) Appl. No.: 10/279,257

(22) Filed: Oct. 23, 2002

(65) Prior Publication Data

US 2004/0082963 A1   Apr. 29, 2004

(51) Int. Cl.
   *A61M 5/00*  (2006.01)
   *A61F 2/04*  (2006.01)
   *A61B 17/08* (2006.01)
   *A61B 18/18* (2006.01)
   *A61D 1/00*  (2006.01)

(52) U.S. Cl. .............. 604/8; 623/23.65; 623/23.7; 606/153; 606/8; 606/219

(58) Field of Classification Search ............. 604/7, 604/8, 19, 27, 28, 48, 500, 506, 507, 508, 604/264, 523, 533, 538, 540, 909; 606/1, 606/8, 108, 139, 140, 151, 153–9, 201–3, 606/205, 213, 219–220, 228; 128/898–99; 623/11.11, 2, 23.64, 23.65, 23.7, 23.71, 23.75–23.76
See application file for complete search history.

(56) References Cited

U.S. PATENT DOCUMENTS

| 2,108,206 A | 2/1938 | Meeker |
| 2,508,690 A | 7/1948 | Schmerl |
| 3,372,443 A | 3/1968 | Daddona, Jr. |
| 3,395,710 A | 8/1968 | Stratton et al. |
| 3,986,493 A | 10/1976 | Hendren, III |
| 4,057,065 A | 11/1977 | Thow |
| 4,063,561 A | 12/1977 | McKenna |
| 4,133,315 A | 1/1979 | Berman et al. |
| 4,134,405 A | 1/1979 | Smit |
| 4,198,982 A | 4/1980 | Fortner et al. |
| 4,246,893 A | 1/1981 | Berson |

(Continued)

FOREIGN PATENT DOCUMENTS

EP    0 137 878 A1    4/1985

(Continued)

OTHER PUBLICATIONS

Gukovsky-Reicher, S., M.D. et al., *Expandable Metal Esophageal Stents: Efficacy and Safety Review of Current Literature Data and of 53 Stents Placed at Harbor-UCLA Medical Center*, www.medscape.com/viewarticle/423508_print_ pp. 1-20, Medscape General Medicine 4(1), 2003 ©2002 Medscape, downloaded Oct. 9, 2006.

(Continued)

*Primary Examiner*—Patricia Bianco
(74) *Attorney, Agent, or Firm*—Fulwider Patton LLP

(57) ABSTRACT

A bypass conduit assembly is placed in a hollow body organ to route food and liquids past the hollow body organ. A flexible tubular member extends from a narrowed section through the hollow body organ and into either the pylorus or intestines. The tubular member is connected to tissue by fasteners such as clips, staples or stents.

6 Claims, 16 Drawing Sheets

U.S. PATENT DOCUMENTS

| | | | |
|---|---|---|---|
| 4,258,705 A | 3/1981 | Sorensen et al. | |
| 4,311,146 A | 1/1982 | Wonder | |
| 4,315,509 A | 2/1982 | Smit | |
| 4,343,066 A | 8/1982 | Lance | |
| 4,402,445 A | 9/1983 | Green | |
| 4,416,267 A | 11/1983 | Garren et al. | |
| 4,458,681 A | 7/1984 | Hopkins | |
| 4,485,805 A | 12/1984 | Foster, Jr. | |
| 4,501,264 A | 2/1985 | Rockey | |
| 4,547,192 A | 10/1985 | Brodsky et al. | |
| 4,558,699 A | 12/1985 | Bashour | |
| 4,592,339 A | 6/1986 | Kuzmak et al. | |
| 4,592,354 A | 6/1986 | Rothfuss | |
| 4,598,699 A | 7/1986 | Garren et al. | |
| 4,607,618 A | 8/1986 | Angelchik | |
| 4,610,383 A | 9/1986 | Rothfuss et al. | |
| 4,636,205 A | 1/1987 | Steer | |
| 4,641,653 A | 2/1987 | Rockey | |
| 4,643,169 A | 2/1987 | Koss et al. | |
| 4,646,722 A | 3/1987 | Silverstein et al. | |
| 4,648,383 A | 3/1987 | Angelchik | |
| 4,671,287 A | 6/1987 | Fiddian-Green | |
| 4,694,827 A | 9/1987 | Weiner et al. | |
| 4,716,900 A | 1/1988 | Ravo et al. | |
| 4,723,547 A | 2/1988 | Kullas et al. | |
| 4,739,758 A | 4/1988 | Lai et al. | |
| 4,744,363 A | 5/1988 | Hasson | |
| 4,773,393 A | 9/1988 | Haber et al. | |
| 4,790,294 A | 12/1988 | Allred, III et al. | |
| 4,803,985 A | 2/1989 | Hill | |
| 4,841,888 A | 6/1989 | Mills et al. | |
| 4,899,747 A | 2/1990 | Garren et al. | |
| 4,905,693 A * | 3/1990 | Ravo | 606/153 |
| 4,925,446 A | 5/1990 | Garay et al. | |
| 4,927,428 A | 5/1990 | Richards | |
| 4,969,474 A | 11/1990 | Schwarz | |
| 5,037,021 A | 8/1991 | Mills et al. | |
| 5,059,193 A | 10/1991 | Kuslich | |
| 5,080,663 A | 1/1992 | Mills et al. | |
| 5,084,061 A | 1/1992 | Gau et al. | |
| 5,112,310 A | 5/1992 | Grobe | |
| 5,129,915 A | 7/1992 | Cantenys | |
| 5,156,609 A | 10/1992 | Nakao et al. | |
| 5,171,233 A | 12/1992 | Amplatz et al. | |
| 5,197,649 A | 3/1993 | Bessler et al. | |
| 5,220,928 A | 6/1993 | Oddsen et al. | |
| 5,222,961 A | 6/1993 | Nakao et al. | |
| 5,226,429 A | 7/1993 | Kuzmak | |
| 5,234,454 A | 8/1993 | Bangs | |
| 5,246,456 A | 9/1993 | Wilkinson | |
| 5,250,058 A | 10/1993 | Miller et al. | |
| 5,254,126 A | 10/1993 | Filipi et al. | |
| 5,259,366 A | 11/1993 | Reydel et al. | |
| 5,259,399 A | 11/1993 | Brown | |
| 5,261,920 A | 11/1993 | Main et al. | |
| 5,263,629 A | 11/1993 | Trumbull et al. | |
| 5,297,536 A | 3/1994 | Wilk | |
| 5,301,658 A | 4/1994 | Zhu et al. | |
| 5,306,300 A | 4/1994 | Berry | |
| 5,309,896 A | 5/1994 | Moll et al. | |
| 5,309,927 A | 5/1994 | Welch | |
| 5,327,914 A | 7/1994 | Shlain | |
| 5,330,486 A | 7/1994 | Wilk | |
| 5,330,503 A | 7/1994 | Yoon | |
| 5,331,975 A | 7/1994 | Bonutti | |
| 5,334,209 A | 8/1994 | Yoon | |
| 5,334,210 A | 8/1994 | Gianturco | |
| 5,345,949 A | 9/1994 | Shlain | |
| 5,346,501 A | 9/1994 | Regula et al. | |
| 5,355,897 A | 10/1994 | Pietrafitta et al. | |
| 5,376,095 A | 12/1994 | Ortiz | |
| 5,382,231 A | 1/1995 | Shlain | |
| 5,403,312 A | 4/1995 | Yates et al. | |
| 5,403,326 A * | 4/1995 | Harrison et al. | 606/139 |
| 5,411,508 A | 5/1995 | Bessler et al. | |
| 5,433,721 A | 7/1995 | Hooven et al. | |
| 5,437,291 A | 8/1995 | Pasricha et al. | |
| 5,449,368 A | 9/1995 | Kuzmak | |
| 5,452,837 A | 9/1995 | Williamson, IV et al. | |
| 5,458,131 A | 10/1995 | Wilk | |
| 5,465,894 A | 11/1995 | Clark et al. | |
| 5,467,911 A | 11/1995 | Tsuruta et al. | |
| 5,486,183 A | 1/1996 | Middleman et al. | |
| 5,489,058 A | 2/1996 | Plyley et al. | |
| 5,503,635 A | 4/1996 | Sauer et al. | |
| 5,527,319 A | 6/1996 | Green et al. | |
| 5,535,935 A | 7/1996 | Vidal et al. | |
| 5,542,949 A | 8/1996 | Yoon | |
| 5,549,621 A | 8/1996 | Bessler et al. | |
| 5,551,622 A | 9/1996 | Yoon | |
| 5,555,898 A | 9/1996 | Suzuki et al. | |
| 5,558,665 A | 9/1996 | Kieturakis | |
| 5,571,116 A | 11/1996 | Bolanos et al. | |
| 5,577,654 A | 11/1996 | Bishop | |
| 5,578,044 A | 11/1996 | Gordon et al. | |
| 5,582,616 A | 12/1996 | Bolduc et al. | |
| 5,584,861 A | 12/1996 | Swain et al. | |
| 5,588,579 A | 12/1996 | Schnut et al. | |
| 5,601,604 A | 2/1997 | Vincent | |
| 5,603,443 A | 2/1997 | Clark et al. | |
| 5,607,094 A | 3/1997 | Clark et al. | |
| 5,624,381 A | 4/1997 | Kieturakis | |
| 5,626,588 A | 5/1997 | Sauer et al. | |
| 5,639,008 A | 6/1997 | Gallagher et al. | |
| 5,649,937 A | 7/1997 | Bito et al. | |
| 5,651,769 A | 7/1997 | Waxman et al. | |
| 5,655,698 A | 8/1997 | Yoon | |
| 5,662,664 A | 9/1997 | Gordon et al. | |
| 5,662,667 A | 9/1997 | Knodel | |
| 5,667,520 A | 9/1997 | Bonutti | |
| 5,676,659 A | 10/1997 | McGurk | |
| 5,676,674 A | 10/1997 | Bolanos et al. | |
| 5,685,868 A | 11/1997 | Lundquist | |
| 5,690,656 A | 11/1997 | Cope et al. | |
| 5,697,943 A | 12/1997 | Sauer et al. | |
| 5,707,382 A | 1/1998 | Sierocuk et al. | |
| 5,722,990 A | 3/1998 | Sugarbaker et al. | |
| 5,728,178 A | 3/1998 | Buffington et al. | |
| 5,735,848 A | 4/1998 | Yates et al. | |
| 5,749,893 A | 5/1998 | Vidal et al. | |
| 5,755,730 A * | 5/1998 | Swain et al. | |
| 5,766,216 A | 6/1998 | Gangal et al. | |
| 5,776,054 A | 7/1998 | Bobra | |
| 5,782,844 A | 7/1998 | Yoon et al. | |
| 5,788,715 A | 8/1998 | Watson, Jr. et al. | |
| 5,792,153 A | 8/1998 | Swain et al. | |
| 5,797,931 A | 8/1998 | Bito et al. | |
| 5,810,851 A | 9/1998 | Yoon | |
| 5,810,855 A | 9/1998 | Rayburn et al. | |
| 5,810,882 A | 9/1998 | Bolduc et al. | |
| 5,816,471 A | 10/1998 | Plyley et al. | |
| 5,820,584 A | 10/1998 | Crabb | |
| 5,824,008 A | 10/1998 | Bolduc et al. | |
| 5,827,298 A | 10/1998 | Hart et al. | |
| 5,833,690 A | 11/1998 | Yates et al. | |
| 5,836,311 A | 11/1998 | Borst et al. | |
| 5,839,639 A | 11/1998 | Sauer et al. | |
| 5,860,581 A | 1/1999 | Robertson et al. | |
| 5,861,036 A | 1/1999 | Godin | |
| 5,868,141 A | 2/1999 | Ellias | |
| 5,868,760 A | 2/1999 | McGuckin, Jr. | |
| 5,876,448 A | 3/1999 | Thompson et al. | |
| 5,879,371 A | 3/1999 | Gardiner et al. | |
| 5,887,594 A | 3/1999 | LoCicero, III | |

| Patent | Date | Inventor(s) |
|---|---|---|
| 5,888,196 A | 3/1999 | Bonutti |
| 5,897,534 A | 4/1999 | Heim et al. |
| 5,897,562 A | 4/1999 | Bolanos et al. |
| 5,906,625 A | 5/1999 | Bito et al. |
| 5,910,105 A | 6/1999 | Swain et al. |
| 5,910,149 A | 6/1999 | Kuzmak |
| 5,921,993 A | 7/1999 | Yoon |
| 5,927,284 A | 7/1999 | Borst et al. |
| 5,928,264 A | 7/1999 | Sugarbaker et al. |
| 5,935,107 A | 8/1999 | Taylor et al. |
| 5,938,669 A | 8/1999 | Klaiber et al. |
| 5,947,983 A | 9/1999 | Solar et al. |
| 5,964,772 A | 10/1999 | Bolduc et al. |
| 5,964,782 A | 10/1999 | Lafontaine et al. |
| 5,972,001 A | 10/1999 | Yoon |
| 5,976,161 A | 11/1999 | Kirsch et al. |
| 5,980,537 A | 11/1999 | Ouchi |
| 5,993,464 A | 11/1999 | Knodel |
| 5,993,473 A | 11/1999 | Chan et al. |
| 6,015,378 A | 1/2000 | Borst et al. |
| 6,030,364 A | 2/2000 | Durgin et al. |
| 6,030,392 A | 2/2000 | Dakov |
| 6,042,538 A | 3/2000 | Puskas |
| 6,044,847 A | 4/2000 | Carter et al. |
| 6,067,991 A | 5/2000 | Forsell |
| 6,074,343 A | 6/2000 | Nathanson et al. |
| 6,083,241 A | 7/2000 | Longo et al. |
| 6,086,600 A | 7/2000 | Kortenbach |
| 6,113,609 A * | 9/2000 | Adams ............... 606/139 |
| 6,119,913 A | 9/2000 | Adams et al. |
| 6,120,513 A | 9/2000 | Bailey et al. |
| 6,136,006 A | 10/2000 | Johnson et al. |
| 6,159,146 A | 12/2000 | El Gazayerli |
| 6,159,195 A | 12/2000 | Ha et al. |
| 6,165,183 A | 12/2000 | Kuehn et al. |
| 6,179,022 B1 | 1/2001 | Schneider et al. |
| 6,179,195 B1 | 1/2001 | Adams et al. |
| 6,186,942 B1 | 2/2001 | Sullivan et al. |
| 6,186,985 B1 | 2/2001 | Snow |
| 6,197,022 B1 | 3/2001 | Baker |
| 6,200,318 B1 | 3/2001 | Har-Shai et al. |
| 6,206,822 B1 | 3/2001 | Foley et al. |
| 6,206,893 B1 | 3/2001 | Klein et al. |
| 6,224,614 B1 | 5/2001 | Yoon |
| 6,231,561 B1 | 5/2001 | Frazier et al. |
| 6,248,058 B1 | 6/2001 | Silverman et al. |
| 6,254,642 B1 | 7/2001 | Taylor |
| 6,273,897 B1 | 8/2001 | Dalessandro et al. |
| 6,279,809 B1 | 8/2001 | Nicolo |
| 6,290,674 B1 | 9/2001 | Roue et al. |
| 6,293,923 B1 | 9/2001 | Yachia et al. |
| 6,302,917 B1 | 10/2001 | Dua et al. |
| 6,312,437 B1 | 11/2001 | Kortenbach |
| 6,328,689 B1 | 12/2001 | Gonzalez et al. |
| 6,338,345 B1 | 1/2002 | Johnson et al. |
| 6,352,543 B1 | 3/2002 | Cole |
| 6,358,197 B1 | 3/2002 | Silverman et al. |
| 6,379,366 B1 | 4/2002 | Fleischman et al. |
| 6,387,104 B1 | 5/2002 | Pugsley, Jr. et al. |
| 6,398,795 B1 | 6/2002 | McAlister et al. |
| 6,416,535 B1 | 7/2002 | Lazarus |
| 6,423,087 B1 | 7/2002 | Sawada |
| 6,432,040 B1 | 8/2002 | Meah |
| 6,447,533 B1 | 9/2002 | Adams |
| 6,460,543 B1 | 10/2002 | Forsell |
| 6,475,136 B1 | 11/2002 | Forsell |
| 6,494,888 B1 | 12/2002 | Laufer et al. |
| 6,506,196 B1 | 1/2003 | Laufer |
| 6,535,764 B2 | 3/2003 | Imran et al. |
| 6,540,789 B1 | 4/2003 | Silverman et al. |
| 6,551,310 B1 | 4/2003 | Ganz et al. |
| 6,554,844 B2 | 4/2003 | Lee et al. |
| 6,558,400 B2 * | 5/2003 | Deem et al. ............... 606/151 |
| 6,561,969 B2 | 5/2003 | Frazier et al. |
| 6,572,629 B2 * | 6/2003 | Kalloo et al. ............... 606/151 |
| 6,579,301 B1 | 6/2003 | Bales et al. |
| 6,592,596 B1 | 7/2003 | Geitz |
| 6,605,037 B1 | 8/2003 | Moll et al. |
| 6,626,899 B2 | 9/2003 | Houser et al. |
| 6,632,227 B2 | 10/2003 | Adams |
| 6,663,598 B1 | 12/2003 | Carrillo, Jr. et al. |
| 6,663,639 B1 | 12/2003 | Laufer et al. |
| 6,663,640 B2 | 12/2003 | Kortenbach |
| 6,675,809 B2 | 1/2004 | Stack et al. |
| 6,682,520 B2 | 1/2004 | Ingenito |
| 6,689,062 B1 | 2/2004 | Mesallum |
| 6,692,485 B1 | 2/2004 | Brock et al. |
| 6,716,222 B2 | 4/2004 | McAlister et al. |
| 6,733,512 B2 | 5/2004 | McGhan |
| 6,736,822 B2 | 5/2004 | McClellan et al. |
| 6,740,098 B2 | 5/2004 | Abrams et al. |
| 6,740,121 B2 | 5/2004 | Geitz |
| 6,746,489 B2 | 6/2004 | Dua et al. |
| 6,754,536 B2 | 6/2004 | Swoyer et al. |
| 6,755,849 B1 | 6/2004 | Gowda et al. |
| 6,755,869 B2 | 6/2004 | Geitz |
| 6,756,364 B2 | 6/2004 | Barbier et al. |
| 6,764,518 B2 | 7/2004 | Godin |
| 6,773,440 B2 * | 8/2004 | Gannoe et al. ............... 606/142 |
| 6,773,441 B1 | 8/2004 | Laufer et al. |
| 6,786,898 B2 | 9/2004 | Guenst |
| 6,790,214 B2 | 9/2004 | Kraemer et al. |
| 6,802,868 B2 | 10/2004 | Silverman et al. |
| 6,821,285 B2 | 11/2004 | Laufer et al. |
| 6,835,199 B2 | 12/2004 | McGuckin, Jr. et al. |
| 6,835,200 B2 | 12/2004 | Laufer et al. |
| 6,837,848 B2 | 1/2005 | Bonner et al. |
| 6,840,423 B2 | 1/2005 | Adams et al. |
| 6,845,776 B2 | 1/2005 | Stack et al. |
| 6,896,682 B1 | 5/2005 | McClellan et al. |
| 6,926,722 B2 | 8/2005 | Geitz |
| 6,966,919 B2 | 11/2005 | Sixto, Jr. et al. |
| 6,981,978 B2 | 1/2006 | Gannoe |
| 6,991,643 B2 | 1/2006 | Saadat |
| 7,020,531 B1 | 3/2006 | Colliou et al. |
| 7,025,791 B2 | 4/2006 | Levine et al. |
| 7,033,378 B2 | 4/2006 | Smith et al. |
| 7,037,343 B2 | 5/2006 | Imran |
| 7,037,344 B2 | 5/2006 | Kagan et al. |
| 7,063,715 B2 | 6/2006 | Onuki et al. |
| 7,083,630 B2 | 8/2006 | DeVries et al. |
| 7,087,011 B2 | 8/2006 | Cabiri et al. |
| 7,097,650 B2 | 8/2006 | Weller et al. |
| 2001/0014800 A1 | 8/2001 | Frazier et al. |
| 2001/0020190 A1 | 9/2001 | Taylor |
| 2001/0037127 A1 | 11/2001 | De Hoyos |
| 2002/0022851 A1 | 2/2002 | Kalloo et al. |
| 2002/0035361 A1 | 3/2002 | Houser et al. |
| 2002/0040226 A1 | 4/2002 | Laufer et al. |
| 2002/0047036 A1 | 4/2002 | Sullivan et al. |
| 2002/0058967 A1 | 5/2002 | Jervis |
| 2002/0072761 A1 | 6/2002 | Abrams et al. |
| 2002/0077661 A1 | 6/2002 | Saadat |
| 2002/0078967 A1 | 6/2002 | Sixto Jr. et al. |
| 2002/0082621 A1 | 6/2002 | Schurr et al. |
| 2002/0143346 A1 | 10/2002 | McGuckin Jr. et al. |
| 2002/0165589 A1 | 11/2002 | Imran et al. |
| 2002/0183768 A1 | 12/2002 | Deem et al. |
| 2002/0193816 A1 | 12/2002 | Laufer et al. |
| 2003/0040804 A1 | 2/2003 | Stack et al. |
| 2003/0040808 A1 | 2/2003 | Stack et al. |
| 2003/0065340 A1 | 4/2003 | Geitz |
| 2003/0065359 A1 | 4/2003 | Weller et al. |
| 2003/0093117 A1 | 5/2003 | Saadat |
| 2003/0109892 A1 | 6/2003 | Deem et al. |
| 2003/0109931 A1 | 6/2003 | Geitz |

| | | | | | | |
|---|---|---|---|---|---|---|
| 2003/0109935 A1 | 6/2003 | Geitz | | 2005/0197684 A1 | 9/2005 | Koch |
| 2003/0120265 A1 | 6/2003 | Deem et al. | | 2005/0198476 A1 | 9/2005 | Gazsi et al. |
| 2003/0120285 A1 | 6/2003 | Kortenbach | | 2005/0203548 A1 | 9/2005 | Weller et al. |
| 2003/0120289 A1 | 6/2003 | McGuckin Jr. et al. | | 2005/0228415 A1 | 10/2005 | Gertner |
| 2003/0132267 A1 | 7/2003 | Adams et al. | | 2005/0256587 A1 * | 11/2005 | Egan ............... 623/23.65 |
| 2003/0158563 A1 | 8/2003 | McClellan et al. | | 2006/0020247 A1 | 1/2006 | Kagen et al. |
| 2003/0158601 A1 | 8/2003 | Silverman et al. | | 2006/0020254 A1 | 1/2006 | Hoffmann |
| 2003/0171760 A1 | 9/2003 | Gambale | | 2006/0020276 A1 | 1/2006 | Saadat et al. |
| 2003/0208209 A1 | 11/2003 | Gambale et al. | | 2006/0036267 A1 | 2/2006 | Saadat et al. |
| 2003/0225312 A1 | 12/2003 | Suzuki et al. | | | | |
| 2004/0006351 A1 | 1/2004 | Gannoe et al. | | FOREIGN PATENT DOCUMENTS | | |
| 2004/0009224 A1 | 1/2004 | Miller | | | | |
| 2004/0010271 A1 | 1/2004 | Kortenbach | | EP | 0 174 843 | 3/1986 |
| 2004/0024386 A1 | 2/2004 | Deem et al. | | EP | 0 246 999 A1 | 11/1987 |
| 2004/0037865 A1 | 2/2004 | Miller | | EP | 0 540 010 | 5/1993 |
| 2004/0039452 A1 | 2/2004 | Bessler | | JP | 63277063 A | 11/1988 |
| 2004/0049209 A1 | 3/2004 | Benchetrit | | JP | 63279854 | 11/1988 |
| 2004/0059349 A1 | 3/2004 | Sixto, Jr. et al. | | JP | 63302863 A | 12/1988 |
| 2004/0059354 A1 | 3/2004 | Smith et al. | | JP | 01049572 A | 2/1989 |
| 2004/0059358 A1 | 3/2004 | Kortenbach et al. | | JP | 04297219 | 10/1992 |
| 2004/0082963 A1 | 4/2004 | Gannoe et al. | | WO | WO 1994/18893 A1 | 9/1994 |
| 2004/0087977 A1 | 5/2004 | Nolan et al. | | WO | WO 99/17662 | 4/1999 |
| 2004/0089313 A1 | 5/2004 | Utley et al. | | WO | WO 1999/17662 A1 | 4/1999 |
| 2004/0092892 A1 | 5/2004 | Kagan et al. | | WO | WO 99/53827 | 10/1999 |
| 2004/0092974 A1 | 5/2004 | Gannoe et al. | | WO | WO 00/32137 | 6/2000 |
| 2004/0097989 A1 | 5/2004 | Molina | | WO | WO 00/48656 | 8/2000 |
| 2004/0107004 A1 | 6/2004 | Levine et al. | | WO | WO 2000/78227 A1 | 12/2000 |
| 2004/0116949 A1 | 6/2004 | Ewers et al. | | WO | WO 2000/78229 A1 | 12/2000 |
| 2004/0122456 A1 | 6/2004 | Saadat et al. | | WO | WO 01/85034 A1 | 5/2001 |
| 2004/0122473 A1 | 6/2004 | Ewers et al. | | WO | WO 2001/66018 A1 | 9/2001 |
| 2004/0122526 A1 | 6/2004 | Imran | | WO | WO 2001/67964 A2 | 9/2001 |
| 2004/0133147 A1 | 7/2004 | Woo | | WO | WO 02/39880 A2 | 11/2001 |
| 2004/0133238 A1 | 7/2004 | Cerier | | WO | WO 02/024080 | 3/2002 |
| 2004/0138525 A1 | 7/2004 | Saadai | | WO | WO 2002/35980 A2 | 5/2002 |
| 2004/0138526 A1 | 7/2004 | Guenst | | WO | WO 2002/071951 A1 | 9/2002 |
| 2004/0138529 A1 | 7/2004 | Wiltshire et al. | | WO | WO 2002/091961 A1 | 11/2002 |
| 2004/0138531 A1 | 7/2004 | Bonner et al. | | WO | WO 02/096327 | 12/2002 |
| 2004/0138682 A1 | 7/2004 | Onuki et al. | | WO | WO 2003/007796 A2 | 1/2003 |
| 2004/0147958 A1 | 7/2004 | Lam et al. | | WO | WO 03/017882 | 3/2003 |
| 2004/0148021 A1 | 7/2004 | Carledge et al. | | WO | WO 2003/078721 A2 | 9/2003 |
| 2004/0148034 A1 | 7/2004 | Kagan et al. | | WO | WO 2003/086247 A1 | 10/2003 |
| 2004/0158331 A1 | 8/2004 | Stack et al. | | WO | WO 2003/088844 A1 | 10/2003 |
| 2004/0162568 A1 | 8/2004 | Saadat et al. | | WO | WO 03/094785 | 11/2003 |
| 2004/0167546 A1 | 8/2004 | Saadat et al. | | WO | WO 2003/099140 A1 | 12/2003 |
| 2004/0172141 A1 | 9/2004 | Stack et al. | | WO | WO 2003/105563 A2 | 12/2003 |
| 2004/0181242 A1 | 9/2004 | Stack et al. | | WO | WO 2003/105671 A2 | 12/2003 |
| 2004/0193190 A1 | 9/2004 | Liddicoat et al. | | WO | WO 2004/009269 A2 | 1/2004 |
| 2004/0220516 A1 * | 11/2004 | Solomon et al. ............... 604/66 | | WO | WO 2004/014237 A1 | 2/2004 |
| 2004/0225183 A1 | 11/2004 | Michlitsch et al. | | WO | WO 2004/017863 | 3/2004 |
| 2004/0225194 A1 | 11/2004 | Smith et al. | | WO | WO 2004/019787 A2 | 3/2004 |
| 2004/0225305 A1 | 11/2004 | Ewers | | WO | WO 2004/019826 | 3/2004 |
| 2005/0049718 A1 * | 3/2005 | Dann et al. ............... 623/23.65 | | WO | WO 2004/037064 | 5/2004 |
| 2005/0055038 A1 | 3/2005 | Kellcher et al. | | WO | WO 2004/049911 A2 | 6/2004 |
| 2005/0055039 A1 | 3/2005 | Burnett et al. | | WO | WO 2004/058102 A2 | 7/2004 |
| 2005/0075622 A1 | 4/2005 | Levine et al. | | WO | WO 2004/060150 A1 | 7/2004 |
| 2005/0075653 A1 | 4/2005 | Saadat et al. | | WO | WO 2004/087014 A2 | 10/2004 |
| 2005/0080444 A1 | 4/2005 | Kraemer et al. | | WO | WO 2004/103189 A1 | 12/2004 |
| 2005/0085787 A1 | 4/2005 | Laufer | | WO | WO 2005/023118 A1 | 3/2005 |
| 2005/0096750 A1 | 5/2005 | Kagan et al. | | WO | WO 2005/037152 A1 | 4/2005 |
| 2005/0119671 A1 | 6/2005 | Reydel et al. | | WO | WO 2005/058239 A2 | 6/2005 |
| 2005/0143760 A1 | 6/2005 | Imran | | WO | WO 2005/060882 A1 | 7/2005 |
| 2005/0148818 A1 | 7/2005 | Mesallum | | WO | WO 2006/078781 A1 | 7/2006 |
| 2005/0149067 A1 | 7/2005 | Takemoto et al. | | | | |
| 2005/0149114 A1 | 7/2005 | Cartledge et al. | | | | |
| 2005/0177176 A1 | 8/2005 | Gerbi et al. | | | | |
| 2005/0194038 A1 | 9/2005 | Brabec et al. | | | | |
| 2005/0194294 A1 | 9/2005 | Oexle et al. | | | | |
| 2005/0194312 A1 | 9/2005 | Niemeyer et al. | | | | |
| 2005/0195925 A1 | 9/2005 | Traber | | | | |
| 2005/0195944 A1 | 9/2005 | Bartels | | | | |
| 2005/0196356 A1 | 9/2005 | Leinen et al. | | | | |
| 2005/0197540 A1 | 9/2005 | Liedke | | | | |
| 2005/0197622 A1 | 9/2005 | Blumenthal et al. | | | | |

OTHER PUBLICATIONS

Benjamin, S.B., et al., *A Double-Blind Cross Over Study of the Garren-Edwards anti-Obesity Bubblem* Abstract Submitted to A/S/G/E/ 1987, Georgetown University Hospital and Fairfax Hospital, Washington, D.C. and Fairfax, VA.

Benjamin, S.B., et al., *Small Bowel Obstruction and the Garren-Edwards Bubble, Lessons to be Learned?* Abstracts Submitted to A/S/G/E/ 1987, Division of Gastroenterology, Department of Medicine, Georgetown University Hospital, Washington, D.C.

Boyle, Thomas M., M.D., et al., *Small Intestinal Obstruction Secondary to Obturation by a Garren Gastric Bubble*, The American Journal of Gastroenterology, vol. 82, No. 1, pp. 51-53, 1987.

Büchler, M.W., M.D. et al., *A Technique For Gastroplasty As A Substitute For The Esophagus: Fundus Rotation Gastroplasty*, Journal Of The American College Of Surgeons, vol. 182, pp. 241-245, Mar. 1996.

Cass, O.W., et al., *Long-Term Follow Up of Patients With Percutaneous Endoscopic Gastrostomy (PEG)*, Abstracts Submitted to A/S/G/E 1987, Department of Medicine, Hennepin County Medical Center, Minneapolis, MN 55415.

Chang, Craig G. M.D., et al., *Gastro-Clip® Gastroplasty: A Very Long-Term Complication*, Obesity Surgery, 14, ©FD-Communications Inc.,2004.

Clark, Charlene, R.N., *The Gastric Bubble: Medicine, Magic or Mania?* SGA Journal, vol. 9, No. 2, pp. 45-47, Fall 1986.

Cummings, David E., M.D., et al., *Plasma Ghrelin Levels After Diet-Induced Weight Loss or Gastric Bypass Surgery*, New England Journal of Medicine, vol. 346, No. 21, pp. 1623-1630, May 23, 2002.

Davenport, Horace W., Ph.D., D.Sc., Physiology of the Digestive Tract: An Introductory Text, 3d Ed., Cover and Table of Contents.

DeMeester, Tom T., M.D., *Evolving Concepts of Reflux: The Ups and Downs of the LES*, Canadian Journal of Gastroenterology, vol. 16, No. 5, pp. 327-331, 2002.

De Waele, B., M.D., et al., *Intragastric Balloons for Preoperative Weight Reduction*, Obesity Surgery, vol. 10, pp. 58-60, 2000.

Edell, Steven L., et al., *Radiographic Evaluation of the Garren Gastric Bubble*, American Journal of Radiology, vol. 145, pp. 45-50, Jul. 1985.

Endo Gia* Universal, Single UseStapler and Endo GIA Roticulator*, Brochure, 8 pages, Undated.

Filipi, Charles J. M.D., et al., Transoral, *Flexible Endoscoping Suturing For Treatment Of GERD: A Mulitcenter Trial*, Gastrointestinal Endoscopy, vol. 53, No. 4, pp. 416-422, 2001.

Gray, Henry, R.R.S., Anatomy of the Human Body, *The Digestive System*, Thirtieth American Edition, pp. 1466-1467, (Undated).

Guidant, Internet. AXIUS™ VACUUM 2 Stabilizer Systems, Internet Website-www.guidant.com/products/axius_vacuum.shtml, 8 pages, visited May 27, 2003.

Hepworth, Clive C. FRCS et al., *Mechanical Endoscopic Methods Of Haemostasis For Bleeding Peptic Ulcers: A Review*, Bailliere's Clinical Gastroenterology, vol. 14, No. 3 pp. 467-476, 2000.

Ikeda, Y. et al., *New Suturing Device For Transanal Endoscopic Microsurgery*, Blackwell Science Ltd. p. 1290, 1997.

Johnson & Johnson Gateway™ Endopath 3mm, 5mm and 10mm Diameter Endoscopic Instruments, Internet Website - www.inigateway.com/home.ihtml?loc=USENG&page=viewContent&parentId-0900. . . , 3 pages, visited May 29, 2003.

Kirby, Donald F., *Incomplete Small Bowel Obstruction by the Garren-Edwards Gastric Bubble Necessitating surgical Intervention*, The American Journal of Gastroenterology, vol. 82, No. 3, pp. 251-253, 1987.

Nieben, Ole Gyring, et al., *Intragastric Balloon as an Artifical Bezoar for Treatment of Obesity*, The Lancet, pp. 198-199, Jan. 23, 1982.

Percival, Walter L., M.D., "The Balloon Diet": *A Noninvasive Treatment for Morbid Obesity. Preliminary Report of 1908 Patients*, The Canadian Journal of Surgery, vol. 27, No. 2, pp. 135-136.

Power Medical Interventions Digital and Wireless Medical Technology, Product Innovation: SurgASSIST™, Internet Website - www/pmi2.com/access_flexibility.asp, 6 pages, visited May 29, 2003.

Snowden Pencer, Diamon-Flex Angled Snake Retractor (class 1,878.4800), Appendix F.f, Undated.

Stoltenberg, P.H., et al., *Intragastric Balloon Therapy of Obesity: A Randomized Double-Blind Trial*, Abstracts of Papers 1985, Scott & White Clinic, Texas A&M College of Medicine, Temple, Texas.

Swain, C. Paul, M.D. et al., *An Endoscopic Sewing Machine*, Gastrointestinal Endoscopy, vol. 32, No. 1 pp. 36-38 1986.

Swain, C. Paul, M.D., *Endoscopic Sewing And Stapling Machines*, Endoscopy pp. 205-210 © Georg Thieme Verlag Stuttgart, New York, 1997.

Swain, C. Paul, M.D., et al., *An Endoscopic Sewing Machine*, Gastrointestinal Endoscopy, vol. 32, No. 1, pp. 36-38, 1986.

Swain, C. Paul, M.D., et al., *An Endoscopic Stapling Device: The Development Of A New Flexible Endoscopically Controlled Device For Placing Multiple Transmural Staples In Gastrointestinal Tissue*, Gastrointestinal Endoscopy, vol. 35, No. 4, pp. 338-339, 1989.

Swain, C. Paul, M.D., *Endoscopic Suturing*. Bailliere's Clinical Gastroenterology, Bailliere's Tindall,, vol. 13 No. 1, pp. 97-108, 1999.

Taylor, T. Vincent, et al., *Gastric Balloons for Obesity*, The Lancet, Abstract, Mar. 27, 1982.

Vandenplas, Y., et al., *Intragastric Balloons in Adolescents With Morbid Obesity*, European Journal of Gastroenterology & Hepatology, vol. 11, No. 3, pp. 243-245, 1999.

Villar, Hugo, V., M.D., *Mechanisms of Satiety and Gastric Emptying After Gastric Partitioning and Bypass*, Surgery, pp. 229-236, Aug. 1981.

Wullstein, C., et al., *Compression Anastomosis (AKA-2) in Colorectal Surgery: Results in 442 Consecutive Patients*, British Journal of Surgery 2000, pp. 1071-1075.

* cited by examiner

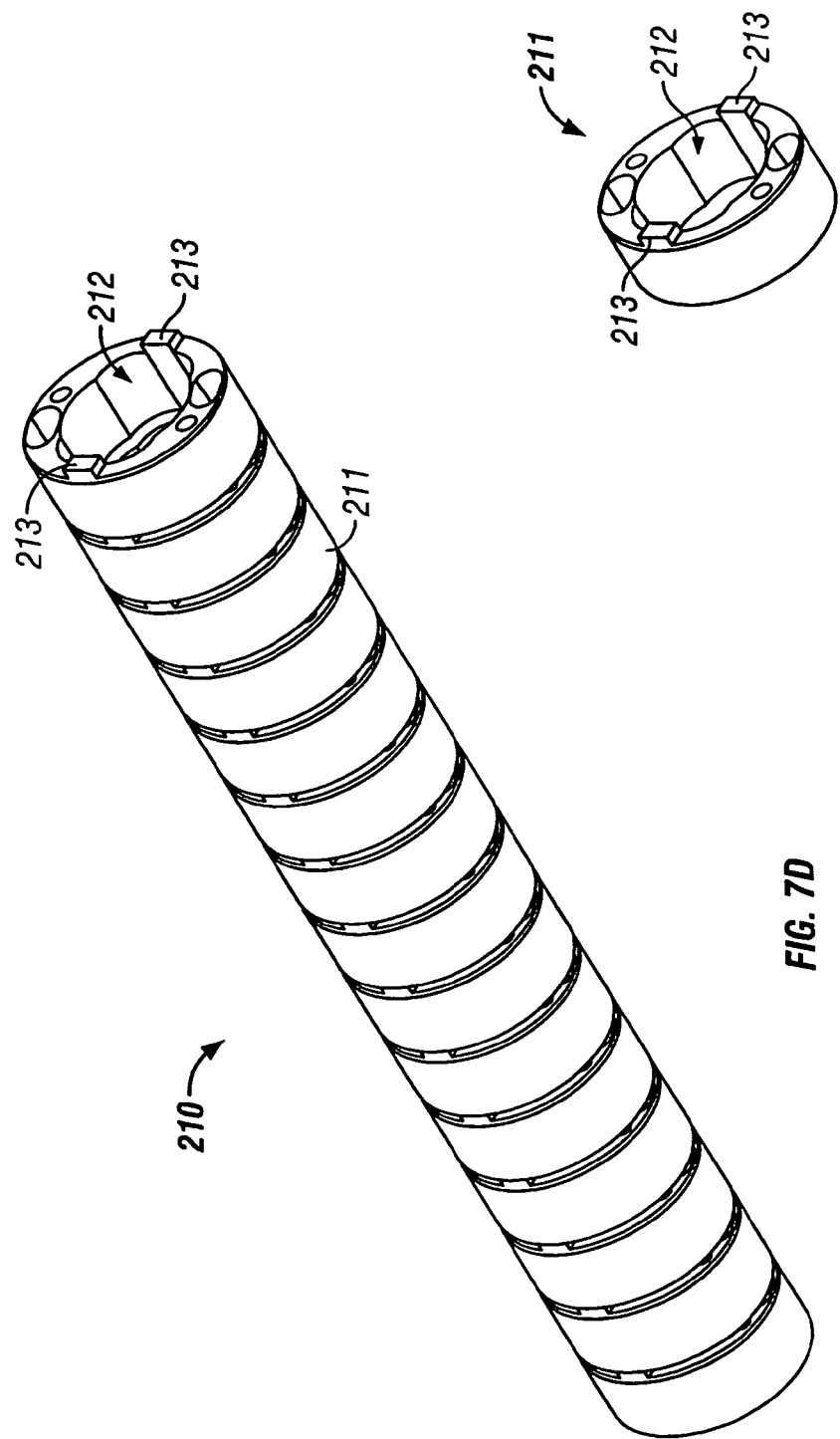

METHOD AND DEVICE FOR USE IN ENDOSCOPIC ORGAN PROCEDURES

FIELD OF THE INVENTION

The present invention relates generally to medical apparatus and methods and more particularly to devices and methods for dividing a hollow body organ or otherwise restricting or partitioning a certain section of that organ, such as a stomach, intestine or gastrointestinal tract.

BACKGROUND OF THE INVENTION

In cases of severe obesity, patients may currently undergo several types of surgery either to tie off or staple portions of the large or small intestine or stomach, and/or to bypass portions of the same to reduce the amount of food desired by the patient, and the amount absorbed by the gastrointestinal tract. The procedures currently available include laparoscopic banding, where a device is used to "tie off" or constrict a portion of the stomach, vertical banded gastroplasty (VBG), or a more invasive surgical procedure known as a Roux-En-Y gastric bypass to effect permanent surgical reduction of the stomach's volume and subsequent bypass of the intestine.

Typically, these stomach reduction procedures are performed surgically through an open incision and staples or sutures are applied externally to the stomach or hollow body organ. Such procedures can also be performed laparoscopically, through the use of smaller incisions, or ports, through trocars and other specialized devices. In the case of laparoscopic banding, an adjustable band is placed around the proximal section of the stomach reaching from the lesser curve (LC) of the stomach around to the greater curve (GC), thereby creating a constriction or "waist" in a vertical manner between the esophagus (ES) and the pylorus (PY) (See Prior Art FIG. 1). During a VBG (See Prior Art FIG. 2) a small pouch (P) (approximately 20 cc in volume) is constructed by forming a vertical partition from the gastroesophageal junction (GEJ) to midway down the lesser curvature of the stomach by externally applying staples, and optionally dividing or resecting a portion of the stomach, followed by creation of a stoma (ST) at the outlet of the partition to prevent dilation of the outlet channel and restrict intake. In a Roux-En-Y gastric bypass (see Prior Art FIG. 3), the stomach is surgically divided into a smaller upper pouch connected to the esophageal inflow, and a lower portion, detached from the upper pouch but still connected to the intestinal tract for purposes of secreting digestive juices. A resected portion of the small intestine is then anastomosed using an end-to-side anastomosis to the upper pouch, thereby bypassing the majority of the intestine and reducing absorption of caloric intake and causing rapid "dumping" of highly caloric or "junk foods".

Although the outcome of these stomach reduction surgeries leads to patient weight loss because patients are physically forced to eat less due to the reduced size of their stomach, several limitations exist due to the invasiveness of the procedures, including time, general anesthesia, healing of the incisions and other complications attendant to major surgery. In addition, these procedures are only available to a small segment of the obese population (morbid obesity, Body Mass Index$\geq$40) due to their complications, leaving patients who are considered obese or moderately obese with few, if any, interventional options.

In addition to surgical procedures, certain tools exist for approximating or otherwise securing tissue such as the stapling devices used in the above-described surgical procedures and others such as in the treatment of gastroesophageal reflux (GERD). These devices include the GIA® device (Gastrointestinal Anastomosis device manufactured by Ethicon Endosurgery, Inc. and a similar product by USSC), and certain clamping and stapling devices as described in U.S. Pat. Nos. 5,897,562 and 5,571,116 and 5,676,674, Non-Invasive Apparatus for Treatment of Gastroesophageal Reflux Disease (Bolanos, et al) and U.S. Pat. No. 5,403,326 Method for Performing a Gastric Wrap of the Esophagus for Use in the Treatment of Esophageal Reflux (Harrison et al) for methods and devices for fundoplication of the stomach to the esophagus for treatment of gastro esophageal reflux (GERD). In addition, certain tools as described in U.S. Pat. No. 5,947,983 Tissue Cutting and Stitching Device and Method (Solar et al), detail an endoscopic suturing device (C.R. Bard, Inc., Billerica, Mass.) that is inserted through an endoscope and placed at the site where the esophagus and the stomach meet. Vacuum is then applied to acquire the adjacent tissue, and a series of stitches are placed to create a pleat in the sphincter to reduce the backflow of acid from the stomach up through the esophagus. These devices can also be used transorally for the endoscopic treatment of esophageal varices (dilated blood vessels within the wall of the esophagus).

Further, certain devices are employed to approximate tissue such as in U.S. Pat. No. 5,355,897 (Pietrafitta) describing the use of a circular stapler to perform a pyloroplasty to create a narrowing at the pylorus. In addition, intraluminal anastomosis, such as bowel anastomosis, use suturing or stapling and employ tools such as the circular stapler, such as that described in U.S. Pat. No. 5,309,927 (Welch), U.S. Pat. No. 5,588,579 (Schnut et al), U.S. Pat. No. 5,639,008 (Gallagher et al), U.S. Pat. No. 5,697,943 (Sauer), U.S. Pat. No. 5,839,639 (Sauer), U.S. Pat. No. 5,860,581 (Robertson et al), and U.S. Pat. No. 6,119,913 (Adams et al). Such circular staplers are available from Ethicon Endosurgery, Cincinnati, Ohio (Proximate™ and EndoPath Stealth™ staplers, see www.surgicalstapling-.com), Power Medical Interventions, New Hope, Pa., and United States Surgical, a unit of Tyco Healthcare Group LP, Norwalk, Conn.

There is a need for improved devices and procedures. In addition, because of the invasiveness of most of the surgeries used to treat obesity, and the limited success of others, there remains a need for improved devices and methods for more effective, less invasive hollow organ restriction procedures.

SUMMARY OF THE INVENTION

The present invention provides for improved methods and apparatus for the transoral, or endoscopic, restriction of a hollow body organ, such as the creation of a small stomach pouch. In the case of the present invention, the surgeon or endoscopist may insert devices as described below through the patient's mouth, down the esophagus and into the stomach or intestine as appropriate. The procedure can be performed entirely from within the patient's stomach or other organ, and does not require any external incision. The end result of the procedure is the formation of a variety of organ divisions or plications that serve as barriers or "partitions" or "pouches" that are substantially sealed off from the majority of the organ cavity. For example, in the case of dividing the stomach, the "pouch" or partitions that are created may seal a small portion of the stomach just below the esophagus to allow only small amounts of food or liquid to be consumed by the patient. This pouch or partition will mimic the section of stomach sealed off from the majority of the organ in a traditional obesity surgery heretofore described; however, it can be formed and secured entirely from inside the stomach endoscopically, obviating the need for a prolonged procedure, external incisions, minimizing the risk of infections, and in some cases, general anesthesia.

The methods and tools of the present invention may also be used in treating GERD in that stomach folds just below the esophagus can be acquired and fastened to create a desired "pleat", thereby effectively extending the length of the esophagus and preventing reflux. Preferably, multiple folds of tissue can be acquired to effect this end. Further, features of the present invention would assist in the longevity of the GE Junction (GEJ)/Esophageal pleat as compared to current devices and techniques as the plication would include a more significant amount of muscular tissue. In addition, the devices and methods of the present invention may be used to revise or repair failures seen in current surgical procedures, such as dilation of the pouch and/or stoma (stomata) formed in a traditional Roux-En-Y gastric bypass, or VBG. In these cases, when the stoma dilates or shifts, the tools of the present invention would be useful to circumferentially gather tissue at the site of dilation to narrow it, thereby making the stoma functional again, or by further reducing the volume of an existing pouch which has dilated.

The devices shown and described herein can be used to form a pouch or partition by the approximation and fixation of a circular section of tissue acquired circumferentially from the walls of the target organ. The tissue acquisition device and fastener may include an acquisition feature (utilizing, e.g., a vacuum, and/or some other mechanical method for acquiring a circumferential "bite" of tissue), a fixation element (such as a stapling mechanism) and possibly a cutting element. In addition, the device may be adapted to receive a standard endoscope to allow viewing of the target region at various points during the procedure. The devices may be articulatable through a variety of conventional methods; alternatively, they may be articulated by a endoscope or other articulation device inserted within.

The fastening assembly of the present invention may employ a similar design and function to those circular staplers heretofore referenced, taking advantage of their ability to deploy multiple rows of staples with one actuation, and their relative clinical efficacy in performing other types of fastening (e.g. anastomoses procedures, hemorrhoid plication, etc.). Such devices can be adapted to perform the novel procedures described herein. Such devices may be adapted to incorporate a tissue acquisition system within the stapler body to allow sufficient tissue to be acquired during a procedure, and other modifications may be done to enable use of the stapler in these novel procedures.

In the procedures of the present invention relating to treatment of gastric disorders such as gastroesophageal reflux disease (GERD), or in cases of treating obesity, a flexible circular stapler may be inserted transorally down the patient's esophagus and into the stomach at the region of the GEJ. Tissue may then be acquired circumferentially about the stapler device, or at least partially about the circumference of the stapler device at some point less than 360 degrees (possibly in a 180 degree formation) relative to a longitudinal axis of the device such that the tissue acquisition creates a "waist" within the organ volume. Subsequently, the tissue fixation element may then be deployed to fix the tissue in a manner to promote healing.

As set forth in U.S. patent application Ser. No. 10/188,547 filed Jul. 2, 2002, which is fully incorporated herein by reference in its entirety, the layered tissue structure of, e.g., the stomach, and the amount of desirable tissue acquisition and approximation is described in further detail. The devices and procedures of the present invention would allow the operator to reliably acquire and secure the necessary type of tissue, such as the muscularis, in creating the circumferential or curved tissue plication desirable to ensure a lasting clinical result.

Any of the fastening devices described herein may employ, e.g., bioabsorbable or biofragmentable staples or fixation element. Such fastening devices would typically dissolve or otherwise degrade leaving only the fixation region once the desired tissue healing has occurred. The remaining healed tissue, now a tissue "ring" (TR), would be sufficiently adhered or healed together to maintain the integrity of the pouch and stoma. In addition, the fastening devices may include coatings or other secondary features to aid healing, such as resorbable meshes, sclerosing agents, surgical felt, or tissue grafts.

The pouch or partitions may be created by a procedure of the present invention to remain permanently within the stomach to restrict it indefinitely. Alternatively, the creation of the pouch or partitions may be reversible (e.g., once weight loss is achieved, or reflux minimized) or revised (in the event pouch side needs to be modified). Reversal can also be achieved via various methods such as dilation of the restricted section, or, e.g., using an electro-surgical device such as a bovie to cut the restricted section to free the tissue folds. Further, if the physician so desires, techniques of the present invention may be augmented or assisted by the use of other techniques such as laparoscopy. Optionally, techniques of the present invention may be combined with other procedures such as for the treatment of GERD or the transoral placement of a bypass prosthesis or other type of liner in the intestine to bypass the hormonally active portion of the small intestine. Such a liner may be tubular in construction and made to match the diameter of the stoma created by the present invention such that they can be hooked together to achieve the desired clinical effect.

BRIEF DESCRIPTION OF THE DRAWINGS

FIGS. 7A–7F show a variation on the circular tissue acquisition and fixation device of the present invention, including details on the inner working elements and flexible shaft thereof;

DETAILED DESCRIPTION OF THE INVENTION

The present invention provides, in part, for methods and devices for hollow organ division and restriction, more particularly providing methods and devices to perform a transoral, endoscopically mediated stomach reduction for purposes of, e.g., treating obesity.

Figure 1:
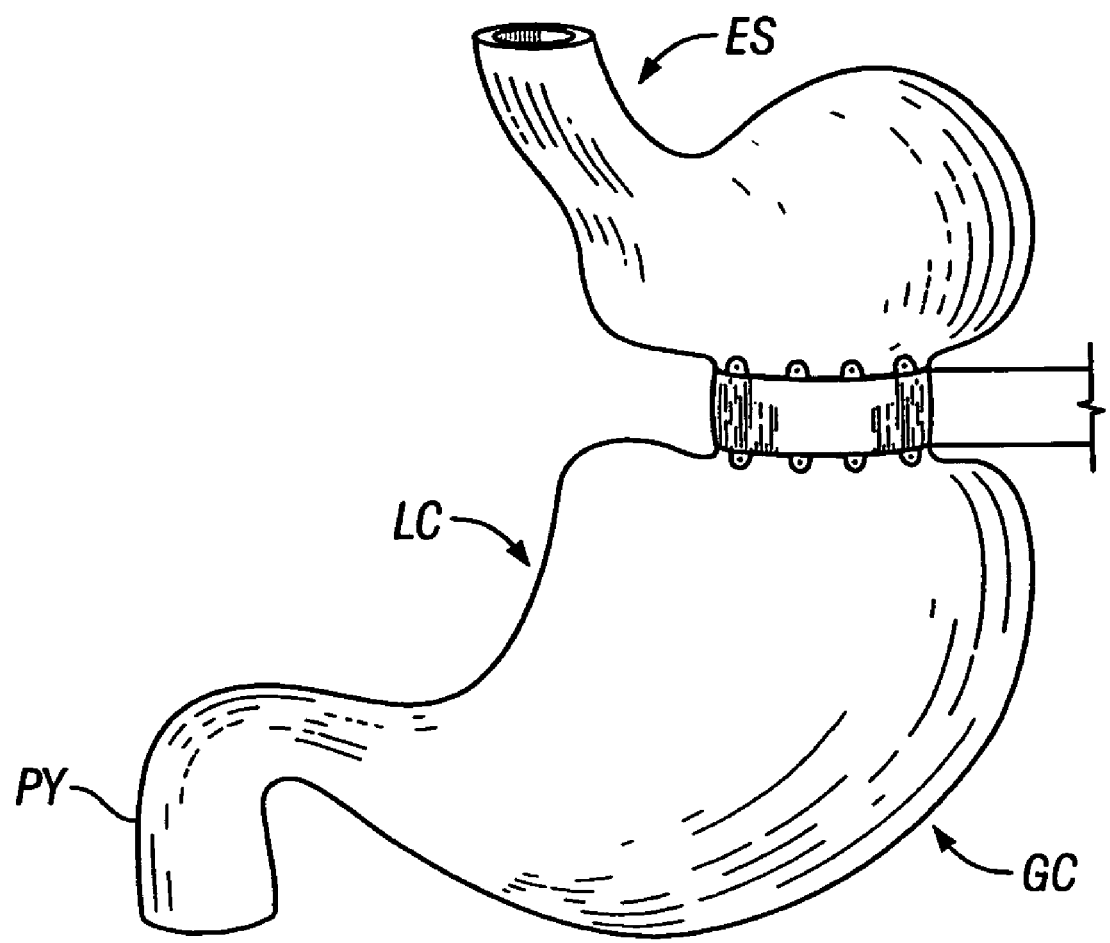
FIG. 1 depicts the prior art procedure commonly known as laparoscopic banding.
Figure 2:
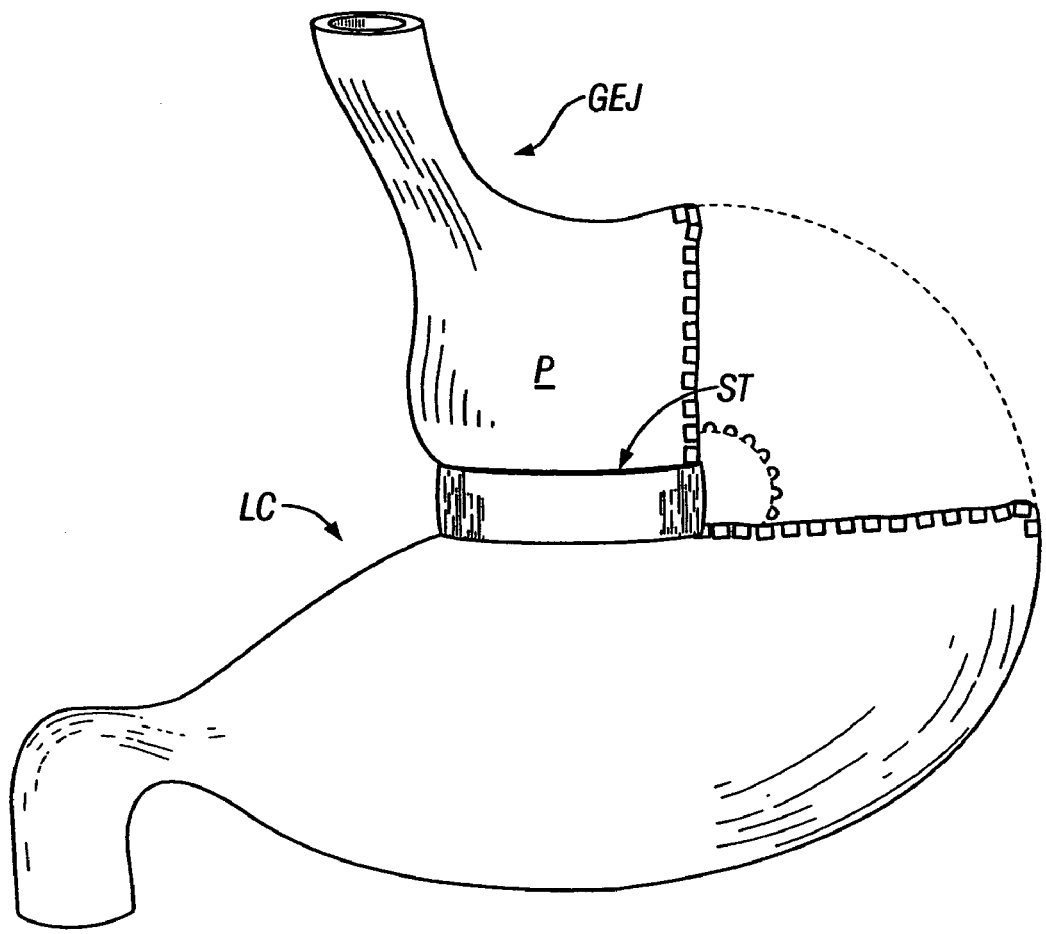
FIG. 2 depicts the prior art procedure commonly known as the vertical banded gastroplasty or "VBG"
Figure 3:
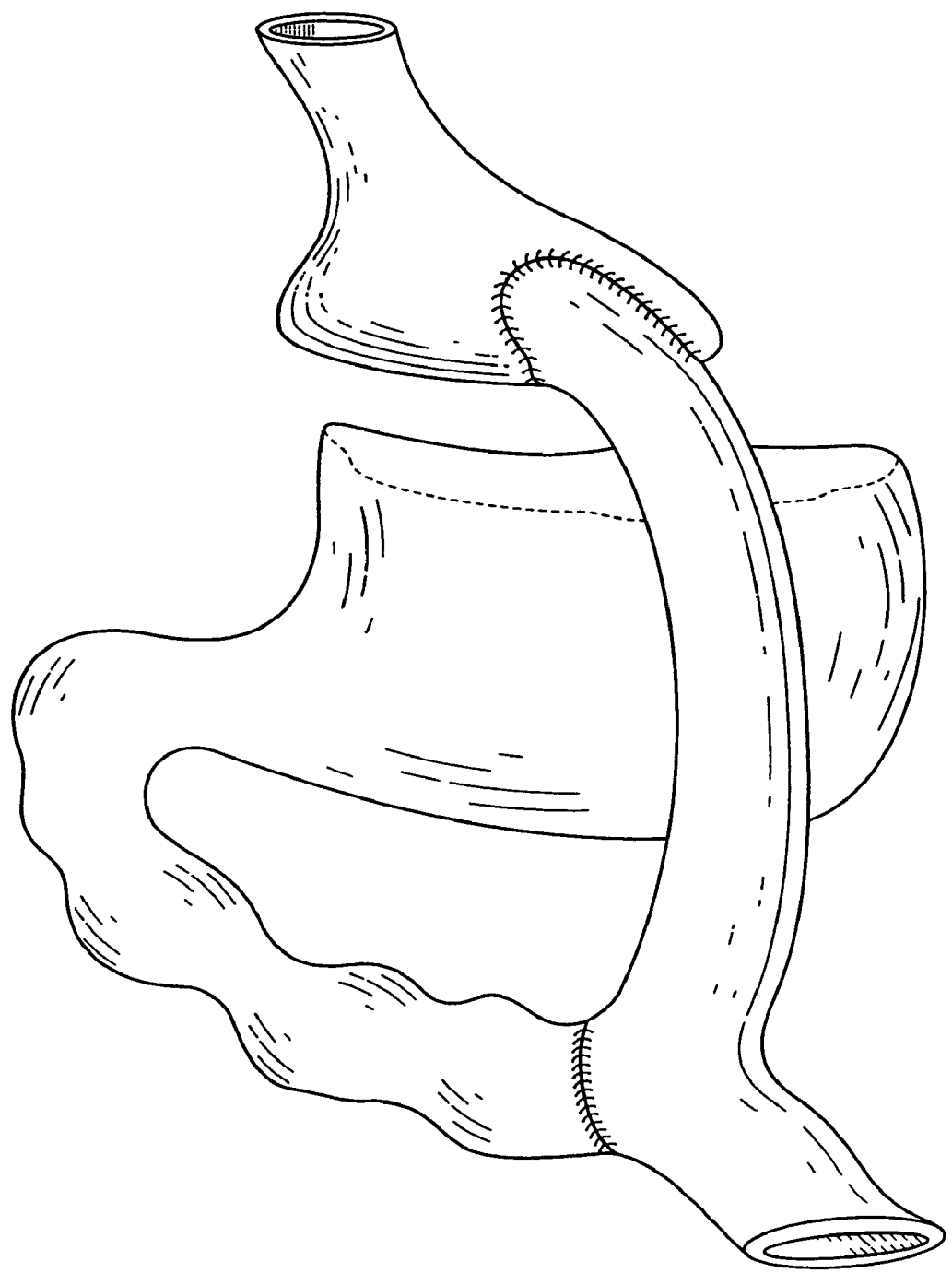
FIG. 3 depicts the prior art procedure commonly know as surgical Roux-En-Y procedure.
Figure 4A:
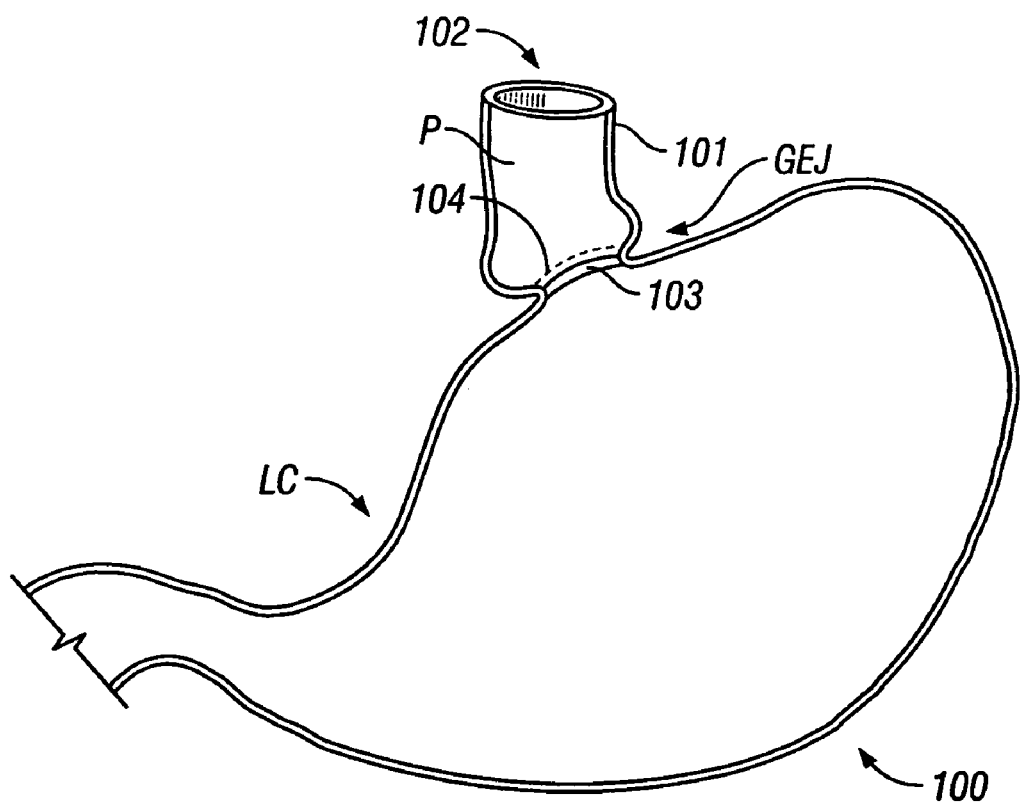
FIGS. 4A–4B depicts one variation on a procedure of the present invention, showing a cut-away section of the tissue being acquired by the distal tip of the device of the present invention, and the resulting modification to the body organ (creation of a "pouch" within the stomach)
Figure 4B:
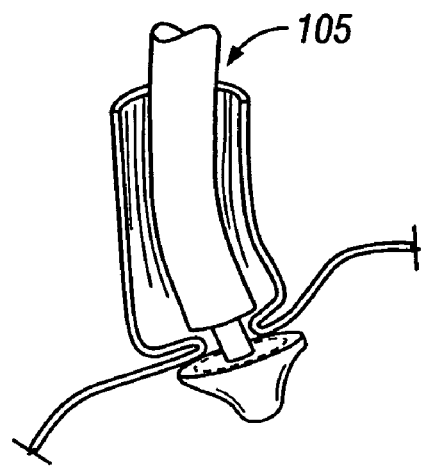

As previously discussed, the results of some clinical procedures of the prior art are shown in FIGS. 1–3, from a perspective external to the stomach. An example of a result of the procedure in one variation of the present invention is shown in FIG. 4A, which depicts an external anterior view of a stomach organ 100, having an esophagus 101 (cut away to reveal the esophageal lumen 102), and further depicting a circumferential orifice or stoma 103, configured from staple line 104, producing a pouch (P). Orifice 103 is preferably positioned close to and on the distal side of the gastroesophageal junction (GEJ) at the base of the esophagus, and angled toward the lesser curve of the stomach (LC), leaving a stoma or opening having a diameter of approximately 1 cm between the pouch (P) and the remaining stomach volume. A desirable pouch (P) volume is between 15–100 cc, preferably 15–20 cc. The orifice 103 operates to restrict food from emptying from the pouch, while still allowing communication between the pouch and the greater stomach volume for purposes of passage of digestive fluids and secretions and absorption of nutrients. FIG. 4B depicts an example of a cross sectional view of the esophagus where it joins the stomach, and further depicts one variation of a tissue acquisition device of the present invention 105, actively engaging the tissue to be fastened in a circumferential fashion.

Method of Hollow Organ Volume Reduction

A clinical work-up, including a physical and mental assessment of the patient may be performed to determine whether a transoral stomach reduction clinically indicated. This assessment may include inspecting the esophagus and stomach of the patient to determine whether any contraindications exist for undertaking the procedure such as ulcerations, obstructions, or other conditions that may preclude treatment. Once the assessment has been completed, either in an operating room with the patient under general anesthesia, or in an endoscopy suite with the patient under sedation, the operator can introduce a tissue acquisition and fixation device, as shown in FIGS. 5A–5D, down the patient's esophagus and into the stomach to a location just beyond the GE Junction (GEJ). Once in place, an optional calibration device (not shown) such as a balloon or bougie can be inflated or deployed proximally or adjacently to the GE Junction (GEJ) to assist in correctly sizing the pouch to be created. Alternatively, the physician may opt to use direct vision and place an endoscope through the main lumen of the tissue acquisition device to view the site of entry and resultant treatment zone.

Figure 5A:
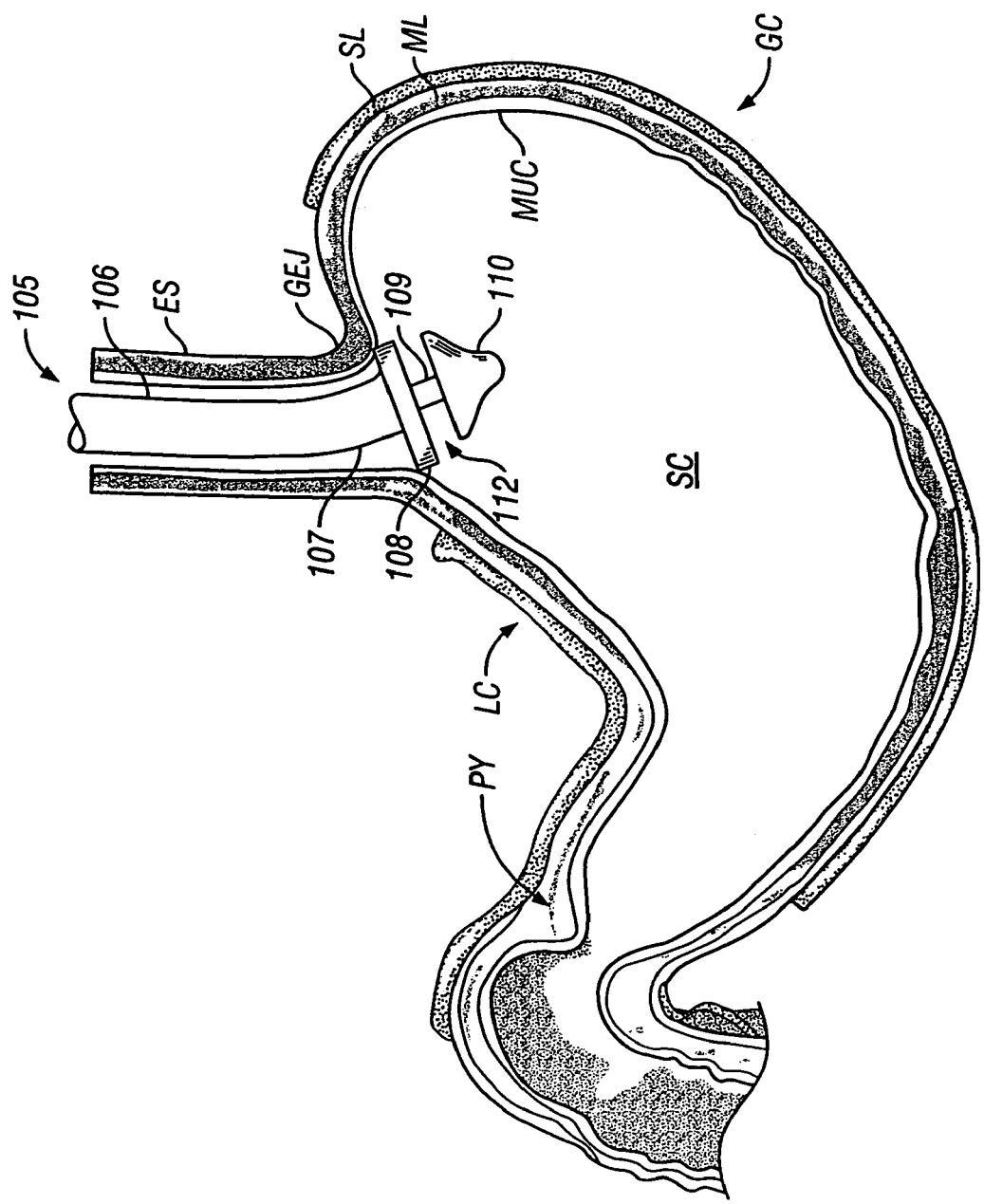
FIGS. 5A–5D depict one variation of procedural steps of performing the methods of the present invention, by showing a cross section of an organ (stomach) and the placement of the device to create a narrowing or "pouch" within the organ.

FIGS. 5A through 5D depict cross sectional schematic views of the procedure of the present invention showing tissue being manipulated within a hollow organ, the stomach. FIG. 5A depicts the esophagus (ES) the stomach cavity (SC), including the landmarks of the lesser curve of the stomach (LC), the gastroesophageal junction (GEJ), and the pylorus (PY). Tissue layers represented are the serosal layer (SL), the muscularis or fibrous muscular layer (ML), and the mucosal layer (MUC). Further, FIG. 5A shows the tissue acquisition device 105 positioned within the esophagus at a location within the stomach cavity (SC) between the lesser curve (LC) of the stomach and the GEJ.

The device 105, includes a main body 106 having at least one lumen therethrough (not shown), an outer portion 107, having a distal end 108 containing a fixation mechanism and a proximal end (not shown). The device 105 further comprises an inner portion 109, which has a distal portion 110 containing a fixation mechanism and a proximal portion (not shown) received therein. Once device 105 is positioned in the preferred anatomical location, outer portion distal end 108 and inner portion distal end 110 are separated by relative movement of inner portion 109 within outer portion 107, to expose opening 112. As described in further detail later below, opening 112 is operatively connected to at least one lumen within the main body 106 and provides a force, e.g., a vacuum force, to facilitate tissue acquisition. Such a force may be provided by a vacuum or by a mechanical element.

Figure 5B:
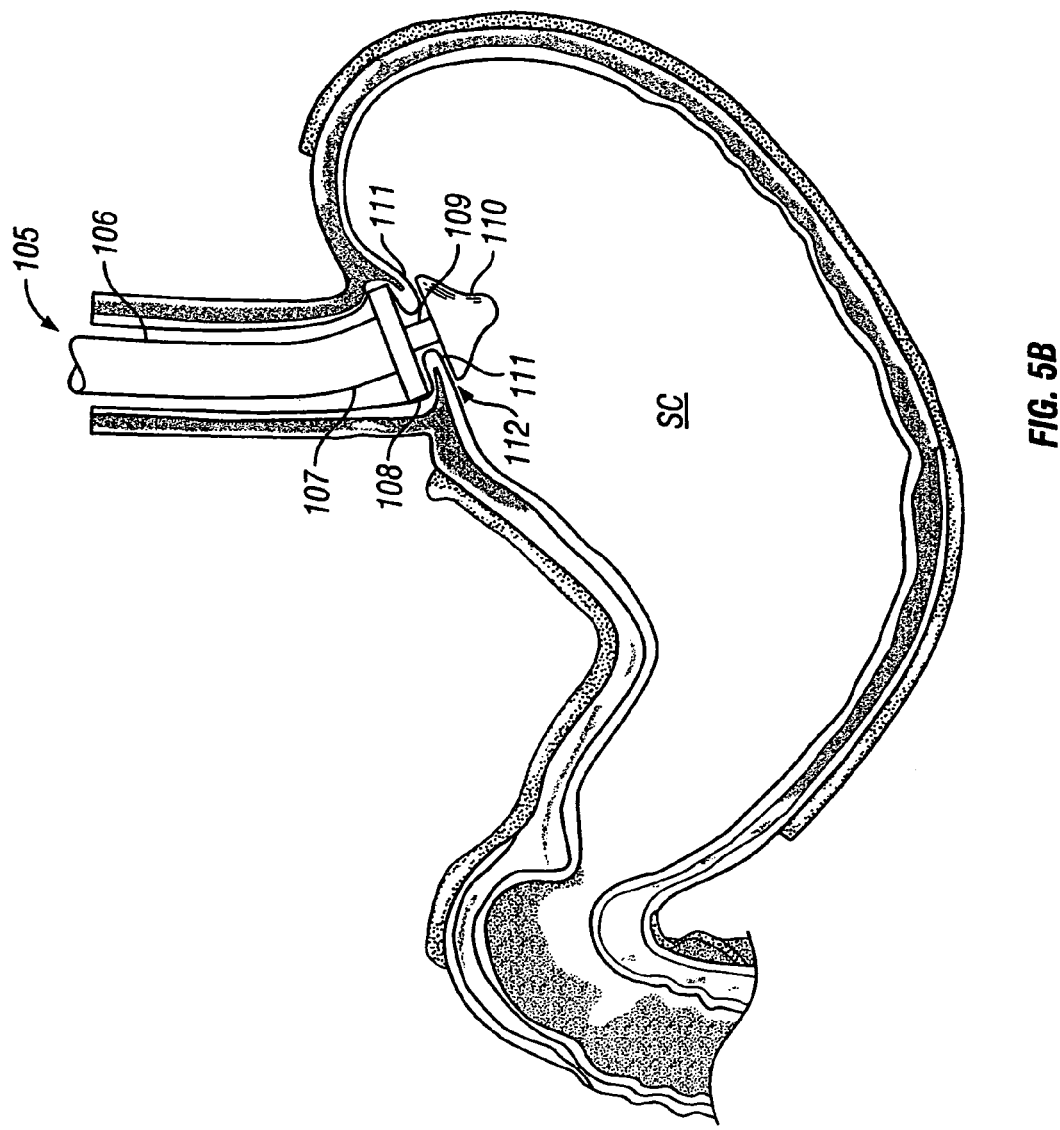

As shown in FIG. 5B, in the case of vacuum, once the opening 112 is exposed to the surrounding tissue within the stomach cavity (SC), the vacuum may be activated and tissue 111 may be drawn into the opening 112 in an entirely circumferential manner or a substantially circumferential manner, i.e., at least partially about the circumference of the device at some point less than 360 degrees (possibly in a 180 degree formation) relative to a longitudinal axis of the device. The amount of tissue 111 acquired can vary, but the amount drawn is preferably sufficient enough to result in healing of the fastened sections, thereby creating a tissue ring (TR) around the circumference of the fastened tissue. Said tissue ring may be formed of various layers of the stomach and may include scar tissue and other elements of effective wound healing.

Figure 5C:
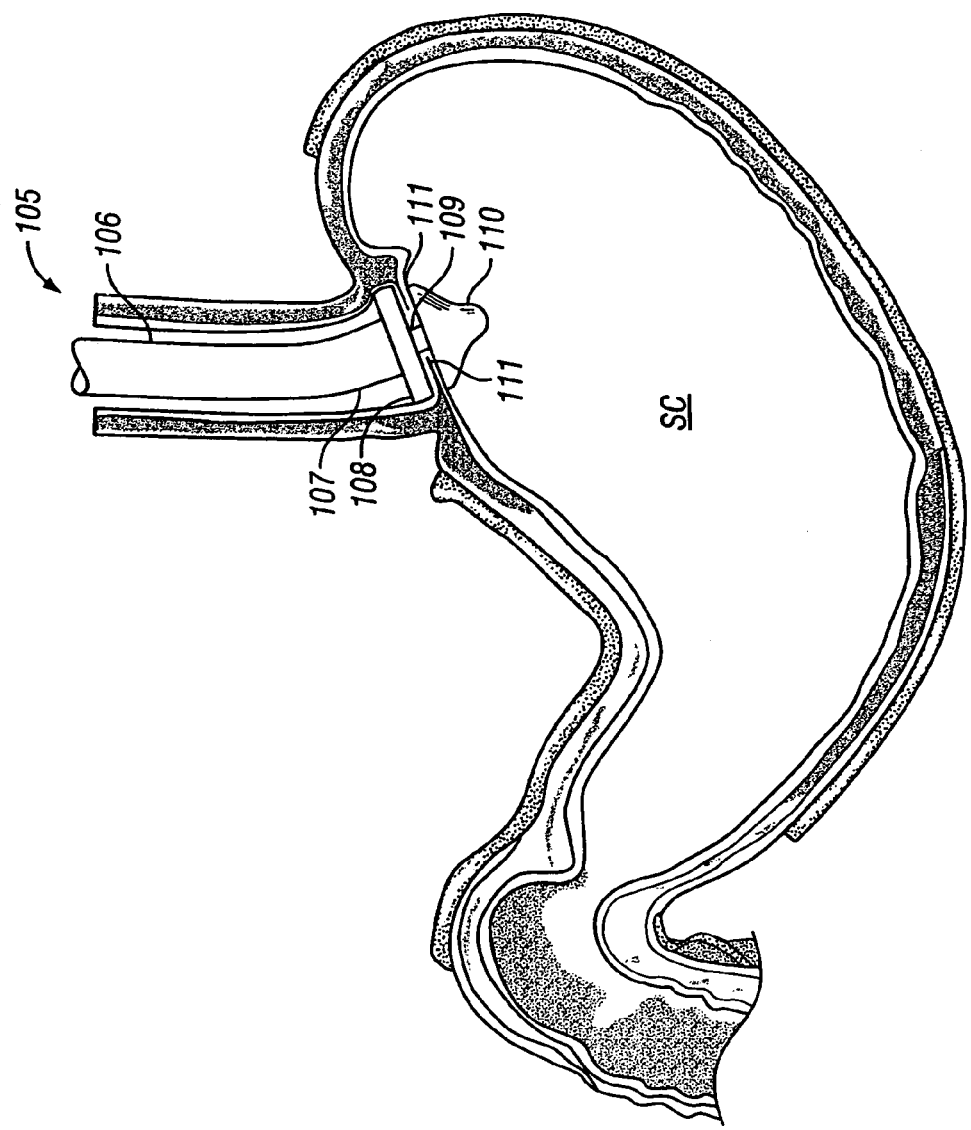
Figure 5D:
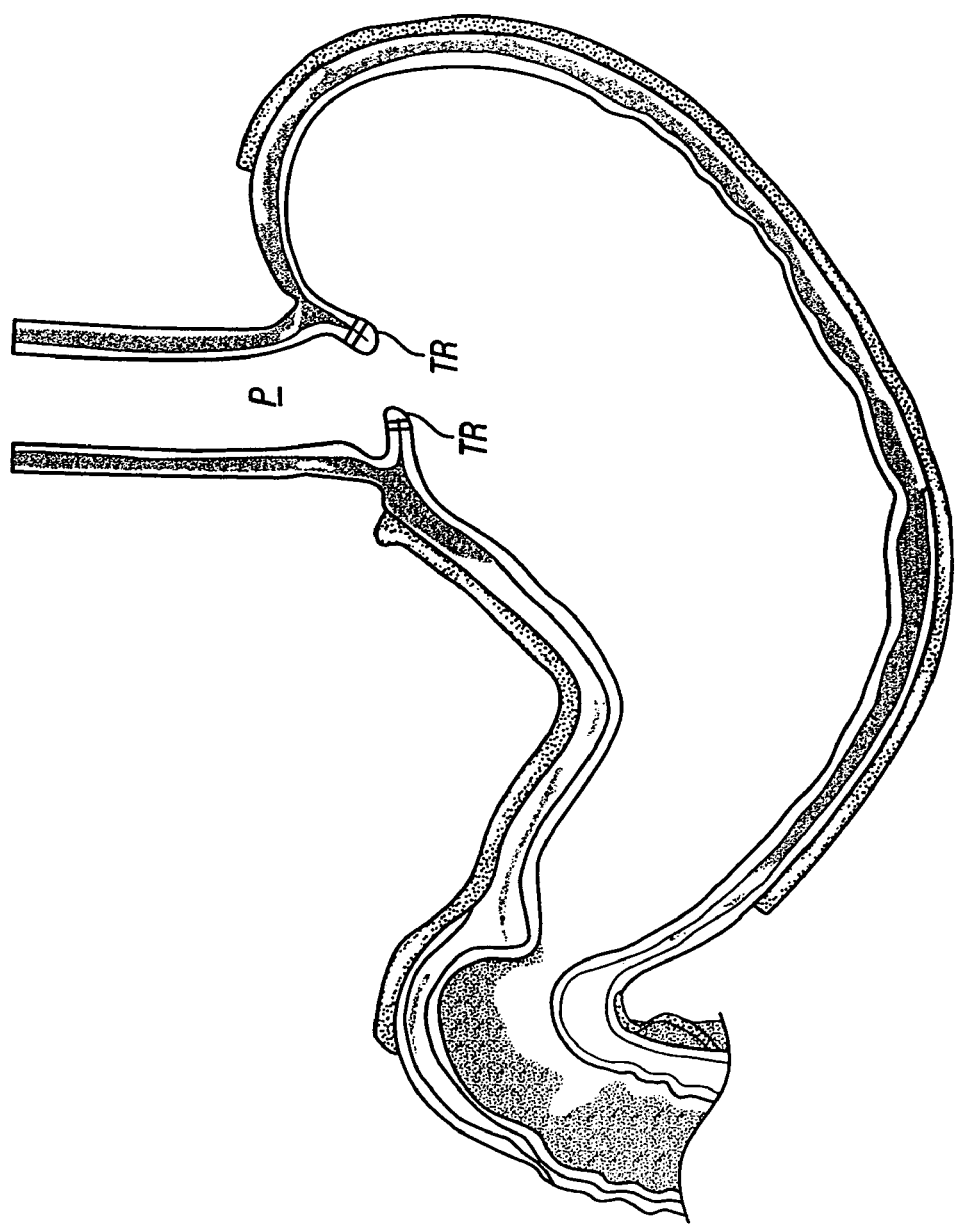

FIG. 5C further depicts the device 105 after the desired amount of tissue 111 has been acquired, outer portion distal end 108 and inner portion distal end 110 may be moved towards one another such that the acquired tissue 111 is clamped therebetween. Device 105 is then actuated to engage at least one fastening element (not shown) through the acquired tissue 111 thereby fastening it in place in a circumferential fashion. This fastening step may also include a cutting step to score or otherwise abrade the acquired tissue 111 after it is fastened to enhance the healing response of the tissue 111 to increase the durability of the tissue ring. In addition, bulking agents, such as collagen, may be injected at the time the stoma is formed, or thereafter, to aid in healing and durability of the tissue. Once the tissue 111 has been fastened or fixed, the tissue acquisition device 105 is then removed. In doing so, the inner portion distal end 110 of the device may be carefully pulled through the newly-created tissue ring or stoma created by the procedure so as to minimize stretching of the ring or stoma. Finally, FIG. 5D depicts the stomach showing the final result and placement of a circumferential tissue ring (TR) or stoma (ST).

Figure 5E:
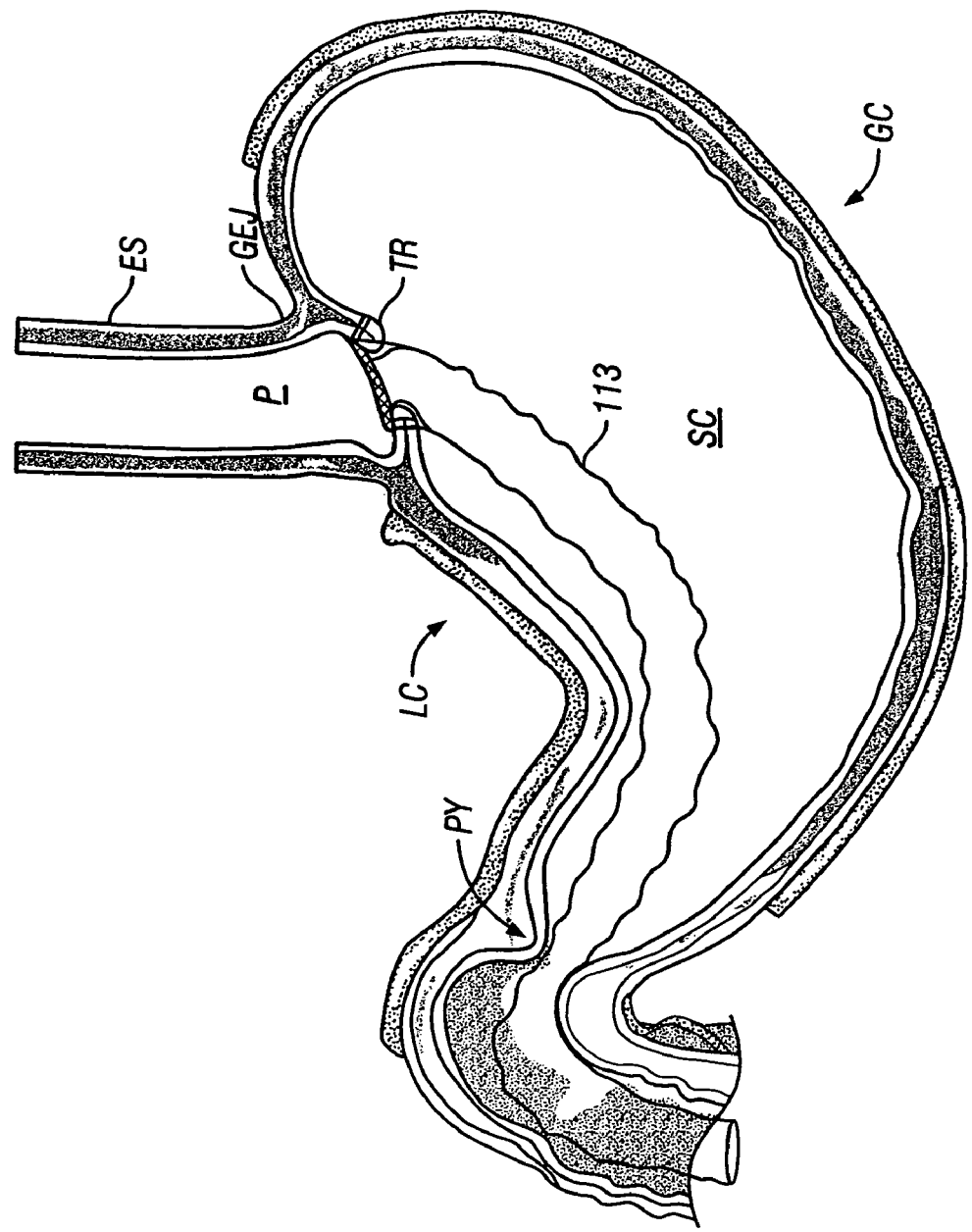
FIG. 5E depicts one variation of a result of the present invention, including a bypassing sleeve installed to bridge from the point of the stoma at the GEJ, to the pylorus, or further into the intestine.

As depicted in FIG. 5E, it is also contemplated that the procedural steps described above may be followed by the placement of an optional bypass conduit 113 to create a bypass from the newly created pouch (P) directly to the pylorus (PY) or beyond into the small intestine. Such a bypass would channel food directly from the pouch (P) into the small intestines to achieve a malabsorptive effect in cases where such an effect may enhance weight loss. Such a bypass conduit 113 may be formed of any suitable biocompatible graft material such as polyester or PTFE, and may be secured to the newly created tissue ring (TR) or stoma (ST) endoscopically using a clip or stent like structure at the anchored end to produce an interference fit within the stoma. Alternatively, the bypass conduit could be placed over the acquisition device of the present invention, and secured by the same fastening elements, and at the same time as the formation of the stoma. In doing so, the end of the bypass graft to be anchored may be placed over the tissue acquisition device such that the end of the graft coincided with the tissue acquisition device opening 112, allowing it to be acquired into the device and fastened along with the surrounding tissue. Similarly, the bypass conduit may be anchored in the pylorus (PY) or intestine by similar methods, or may just be left unanchored in the intestine to allow for movement due to peristalsis of the intestinal wall.

Figures 6A, 6B:
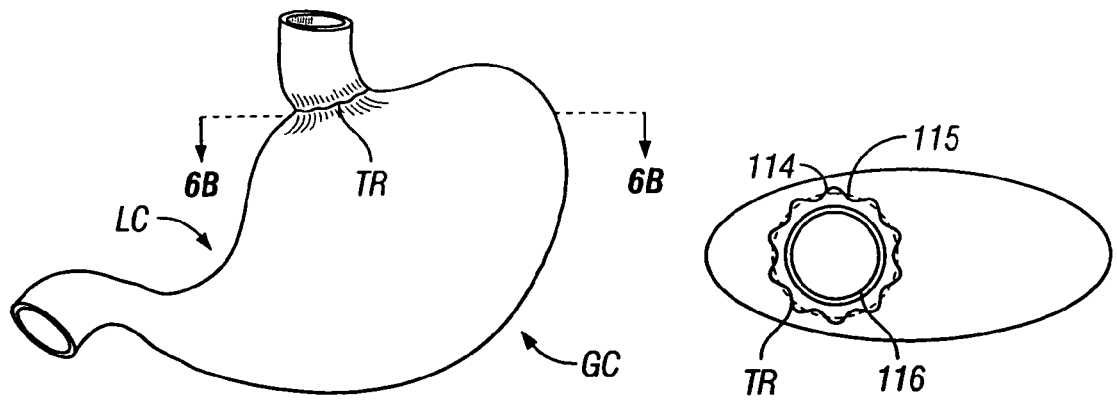
FIGS. 6A–6D shows a schematic depiction of an organ (stomach) following completion of one variation on a procedure of the present invention and the resulting cross sectional view of the treated region in various configurations.
Figure 6C:
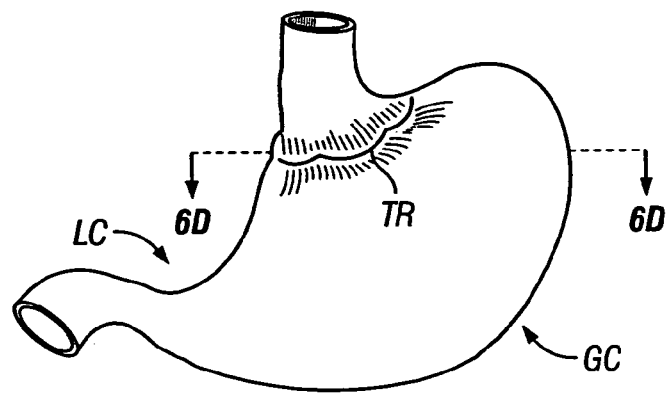
Figure 6D:
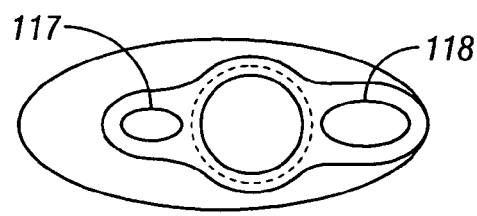

FIGS. 6A–6D depict variations of the tissue rings and pouches created using the method, and variations thereof, described herein. FIGS. 6A and 6B depict the results of utilizing the procedure described above, showing a complete circumferential ring, in this variation, created just distal from the where the esophagus (ES) and the stomach join each other. FIG. 6B shows a cross section of the stomach and tissue ring (TR) and further depicts the resulting tissue folds 114 acquired by the device 105 and the fixation elements 115 deployed to fix the acquired tissue. This cross section further depicts a cut zone or abraded zone 116 as described above. FIGS. 6C and 6D depict another variation in which fixation of the acquired tissue in a position centered between the lesser curve of the stomach (LC) and the greater curve (GC) in such a manner that multiple lumens 117, 118 result as shown in FIG. 6D. Although only two additional lumens 117, 118 are shown in this variation, a number of lumens may be created in other variations depending upon the number of times and positions the tissue is affixed.

One method of the present invention is to use the device 105, or a variation thereof, to modify or otherwise assist in other procedures that utilize stomach or organ plication such as those described in co-pending U.S. patent application Ser. No. 10/188,547 earlier incorporated herein by reference, which describes, in part, in further detail methods and devices for stapling regions of the stomach in a linear fashion. In cases where a zone of the stomach is linearly stapled, the device 105 may be employed to create circular stomas at either end of the linear staple line so as to enhance the efficacy of a volume reduction procedure or to enhance durability of the staple line. It may also be advantageous to place semi-circular or partially circumferential fixation zones at various locations within the target hollow organ. The devices and methods described herein are particularly well-suited for this because of their ability to "gather" the tissue and create a circumferential restriction that acts to limit the flow of matter, such as food, through the organ.

Devices

Figure 7A:
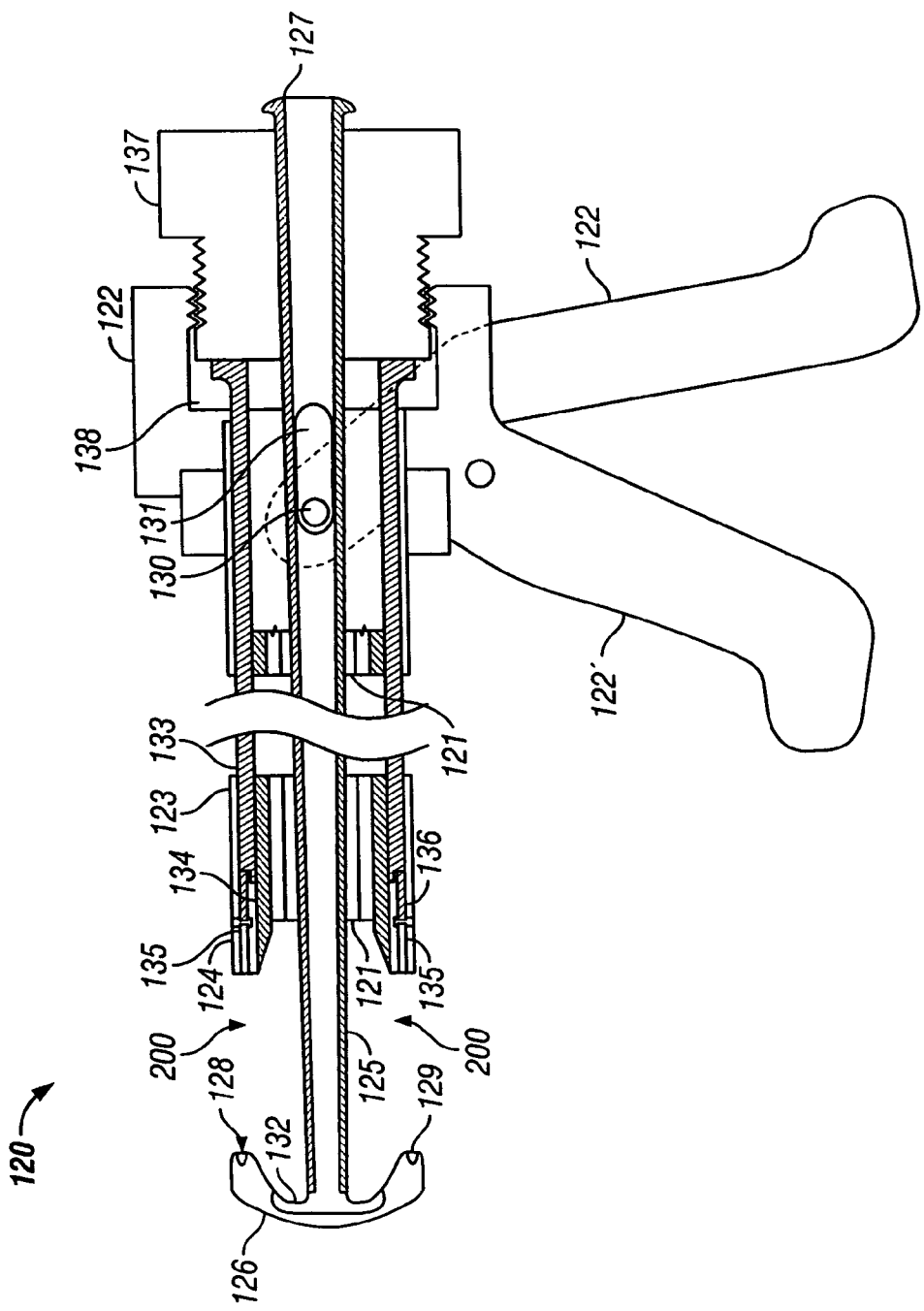

FIG. 7 depicts a cross-sectioned view of one variation of tissue acquisition device 120. As shown, device 120 has a main body portion 123 which has a proximal end, a distal end, and a main lumen 121 defined therethrough. Device 120 also has a grip portion 122' and an opposing handle portion 122 which may be pivotally attached to main body portion 123 such that handle portion 122 is angularly positionable relative to grip portion 122'. Main body portion 123 may further define one or more circumferentially defined lumens along its length such that these lumens terminate at the distal end of body portion 123 at outer distal portion 124. Main body portion 123 further houses main body inner portion 125, which may be an elongate tubular member configured to be slidably positioned within main body lumen 121 defined through the length of main body portion 123. At the distal end of inner portion 125, an inner body distal portion 126 may be attached thereto. This distal portion 126 may be integrally formed onto inner portion 125 or attached separately and may be used as a clamping member to facilitate the mechanical retention of tissue invaginated into the device 120. Distal portion 126 may also function as an anvil for reconfiguring fastening members inserted into the tissue, as further described below. The proximal end of inner portion 125 may terminate proximally of main body portion 123 in a fluid port 127, which may be utilized for fluid connection to, e.g., a vacuum pump (not shown). Alternatively, distal portion 126 may function as the staple housing and outer distal portion 124 may function as the opposing anvil. In this variation, the fasteners, as positioned within distal portion 126, may be deployed through inner face 128 into the tissue using an actuation device, as known in the art.

Figures 7B, 7C:
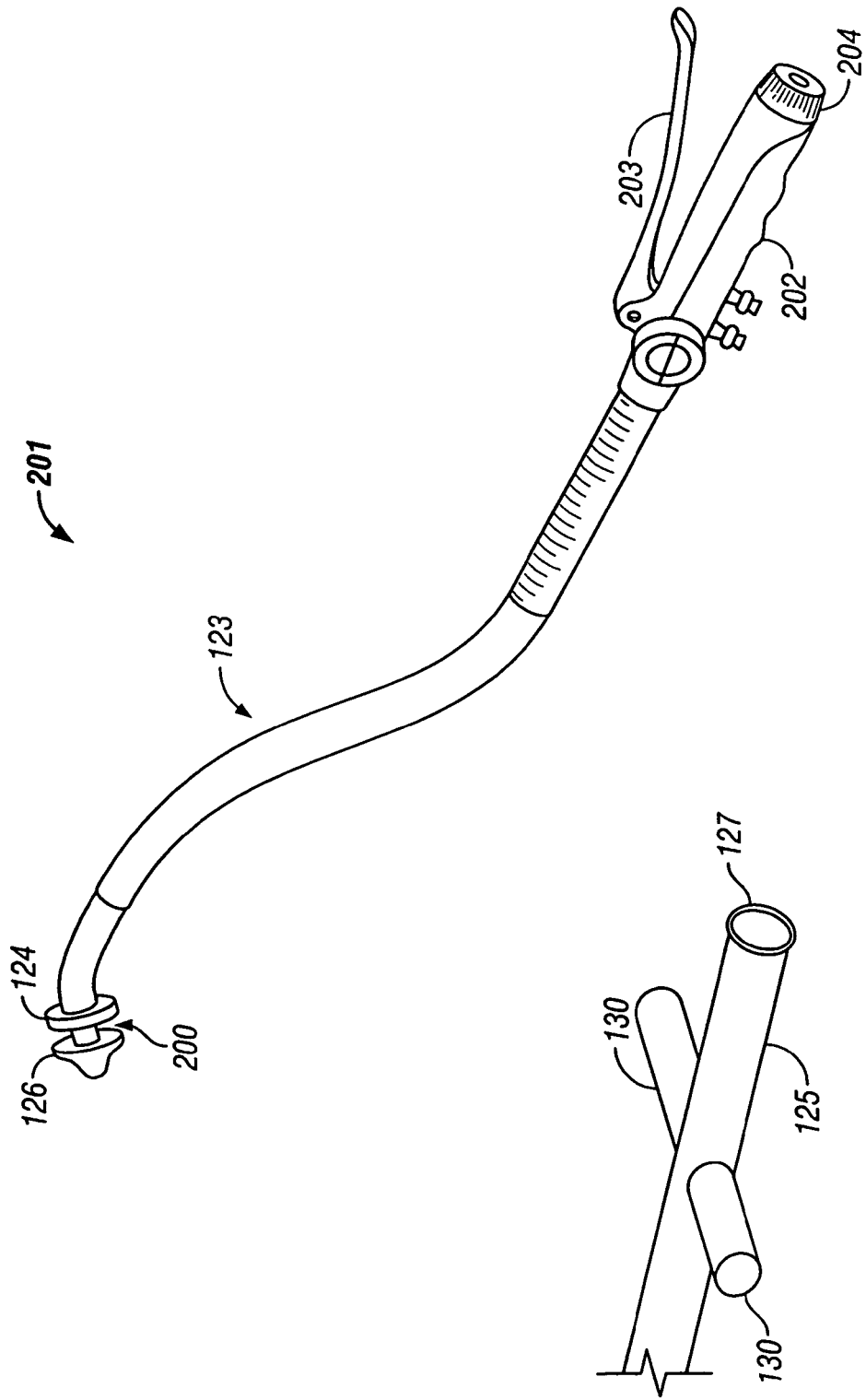

Inner body distal portion 126 may further comprises an inner face 128 which may define an anvil or fastener element detent 129. Where inner portion 125 joins with distal portion 126, one or more distal ports 132 may be defined which are in fluid communication through inner portion 125 with fluid port 127. To actuate device 120, handle portion 122 may be urged to pivot relative to grip portion 122'. Slider pins 130 may be fixedly attached to main body inner portion 125 and configured to extend perpendicularly relative to inner portion 125, as shown in FIG. 7B. Pins 130 may be operatively connected with handle 122 such that rotation or movement of handle 122 is translated into the linear motion of inner portion 125. Pins 130 may be positioned within slot 131 which are defined longitudinally within main body portion 123. Slots 131 may be configured to allow limited translational movement of pins 130 thereby limiting the overall translational distance traveled by inner portion 125.

Actuation of handle 122 in a first direction may urge pins 130 to slide within slots 131 a first direction, e.g., distally, thereby moving inner portion 125 distally, and actuation of handle 122 in a second direction may urge pins 130 to slide in a second direction, e.g., proximally, thereby moving inner portion 125 proximally. Main body inner portion 125 may be actuated to linearly move inner body distal portion 126 relative to outer distal portion 124 to a desired distance between the two. When the two portions 124, 126 are moved into apposition to one another, a circumferential tissue acquisition chamber or space 200 may be created about or defined between the outer surface of inner portion 125, inner distal portion 126, and outer distal portion 124. Space 200 may be in fluid communication with distal port 132 and/or optionally through main body lumen 121. In operation, a vacuum force may be applied through distal port 132 and/or main body lumen 121 to invaginate or draw tissue into space 200 such that the tissue is held or configured to then receive at least one fastening element to affix the tissue configuration.

Main body portion 123 may further house driver element 133 within circumferentially-shaped fastener lumen 134. Driver element 133 may be a tubularly shaped member which is configured to traverse longitudinally within fastener lumen 134. Disposed distally of driver element 133 within fastener lumen 134 are fasteners 135 and fastener pusher mechanism 136. Fasteners 135 may comprise any variety of staples or mechanical fasteners which are made from a biocompatible material, e.g., stainless steel, platinum, titanium, etc., and fastener retention mechanism 136 may also comprise any variety of staple retainer which is configured to hold fasteners 135 within fastener lumen 134 until fasteners 135 have been pushed or urged out of the lumen 134 and into the tissue. The proximal end of driver element 133 abuts driver actuator 137 in handle portion 122. Handle portion 122 may define a threaded cavity 138 at its proximal end which is configured to correspondingly receive and is in operative communication with driver actuator 137, which may also define a threaded insertion surface for mating with threaded cavity 138. In operation, upon tissue acquisition within circumferential space 200 and approximation of main body inner distal portion 126 and main body outer distal portion 124, driver actuator 137 may be rotated in a first direction so as to matingly engage the threads of handle portion threaded cavity 138 and thereby engage the proximal end of driver element 133 to cause driver element 133 to move distally. As driver element 133 is advanced longitudinally in a corresponding manner as driver actuator 137 is rotated, the distal end of driver element 133 may contact fastener pusher mechanism 136 and actuating fastener 135 to distally advance and deploy fastener 135 into any acquired tissue.

Main body portion 123 may be bendable as depicted in FIG. 7C. As shown, the device 201 may be seen in one configuration in which main body portion 123 may be configured in an infinite number of different configurations for negotiating pathways within a body. This particular variation 201 shows handle grip 202 having an opposing actuation handle 203 for actuating movement of inner body distal portion 126. Also shown is an optional scope lumen 204 in the handle 202 which may be used for visualizing the tissue region being treated during deployment or actual treatment. The flexibility of the main body portion 123 may be imparted, in part, by the use of, e.g., linking multiple rings 211, as shown in the isometric view in FIG. 7D. A portion 210 of the main body 123 is shown with the covering, control mechanisms, etc., omitted for clarity. Although this variation shows the use of stacked multiple rings, other variations may also be used as known in the art for flexible and/or articulatable elongate devices, e.g., endoscopes, etc. A plurality of individual rings 211 may be aligned with one another to create a length of the main body portion 123. Any number of rings 211 may be used depending upon the overall desired length of the device or the desired length of a flexible portion of the device. Each of the rings 211 may have at least one main channel or lumen 212, which when individual rings 211 are aligned as a whole, create a main channel throughout the length of the device. Each of the rings 213 may also have a number of spacers or protrusions 213 defined on or around the circumference of the device for creating pivotable sections for facilitating relative motion between adjacent rings 211, as known in the art. Although the rings 211 are shown with two oppositely positioned protrusions 213, any number of protrusions 213 may be used as practicable depending upon the degree of relative motion desired between adjacent rings 211. Alternatively, device main body 123 may be constructed in part of, e.g., a coil spring, to achieve a similar functional result. Coil springs may be made of superelastic materials, e.g., nitinol, or spring steels made, e.g, from stainless steels. The main body 123 or main body segments may be constructed of various biocompatible materials, such as stainless steel, Delrin or other engineering thermoplastics, etc.

FIG. 7E depicts a single ring 211 having the main lumen 212 defined therethrough. Main lumen 212 may be modified and enlarged to provide a channel having a large enough diameter to receive a conventional endoscope for possible use with the present device. One example of such a device may have a lumen diameter of, e.g., 10 mm, with an outer diameter of, e.g., 18 mm. One or more of such lumens may be created within the annular section 211 to enable linkage of each section 211 to one another by one or several cables or flexible wires (not shown) adapted to be positioned through the lumens. These wires or cables may be routed through the length of the device and fixed at the proximal end of the main body portion 123.

Figure 7F:
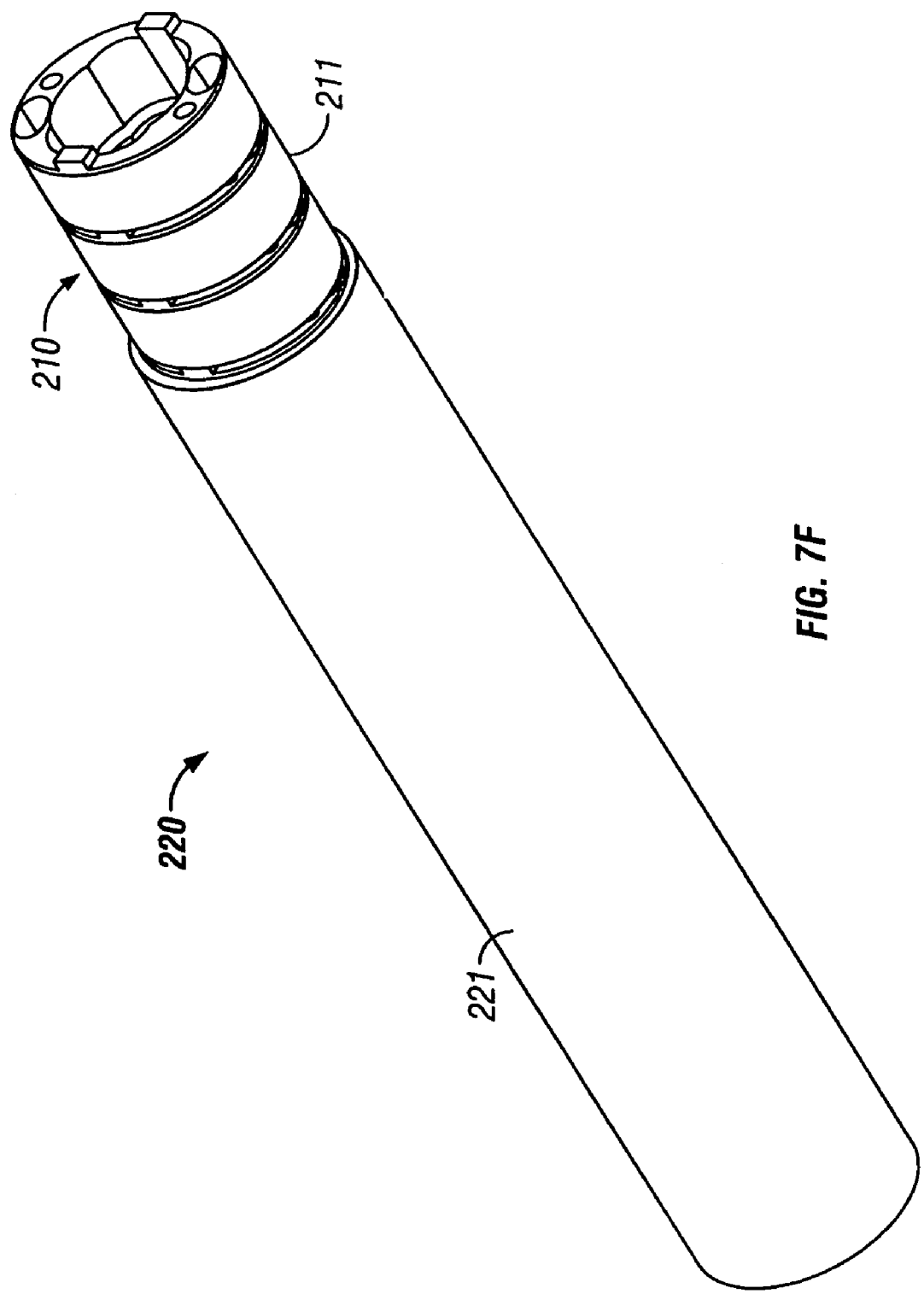

As shown in FIG. 7F, an optional sheath or thin film 221 may be placed over the device or at least along a portion 210 of the device to encapsulate the linkages and create a smooth shaft surface, while still maintaining its flexibility. The sheath or thin film 221 may be made of a variety of biocompatible materials, e.g., heatshrink polymers, plastics, etc.

Figure 8:
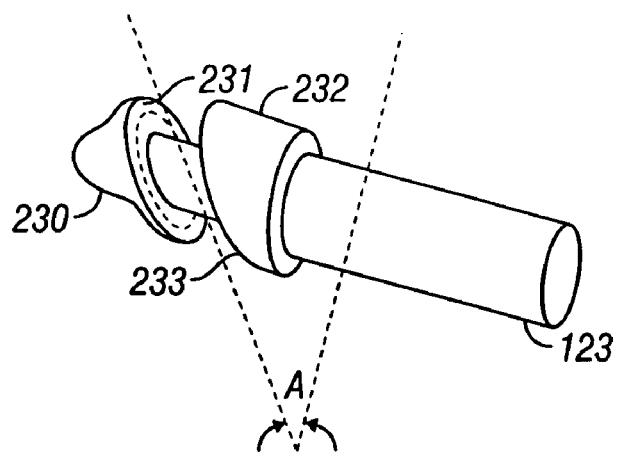
FIG. 8 depicts details of one variation on the distal portion of the circular tissue acquisition and fixation device of the present invention showing an angled annular acquisition space.
Figure 9:
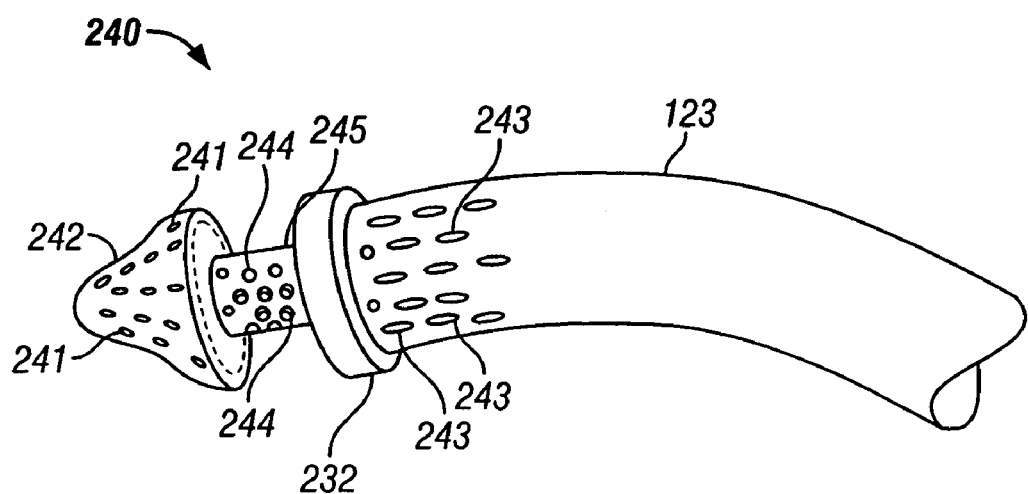
FIG. 9 depicts another variation of the tissue acquisition mechanism of the circular tissue acquisition and fixation device of the present invention.

FIG. 8 depicts another variation on the distal end of a tissue acquisition device. The inner distal portion 230 is shown defining an inner face 231 and device outer distal portion 232 having an inner face 233. The inner distal portion inner face 231 and the outer distal portion inner face 233 may be formed to face one another in apposition and both faces 231, 233 may each be formed at an angle (A) relative to a longitudinal axis of the device main body 123. The angle (A) may range anywhere from 0–90 degrees, but is preferably in the range of 15–45 degrees, depending on the desired angle of the resulting tissue fixation zone. This variation may be used to allow the operator to position the tissue acquisition device perpendicularly to a surface of the organ to be treated (for ease of use) while acquiring and fixing the tissue at an angle relative to the tissue surface. In doing so, the operator may fashion the resulting fixation zone to more closely approximate a curvature of the organ, such as the curvature between the GEJ and the LC of the stomach. FIG. 9 depicts a further variation 240 of the tissue acquisition device in which fenestrations or ports 241 may be defined over the surface of the device inner distal portion 242. Additional fenestrations or ports 243 may be defined over a portion of the device outer distal portion 232, and additional fenestrations or ports 244 may also be defined over a surface of body inner portion 245. These additional ports may allow this variation 240 to acquire tissue along a length of the distal end of the tissue acquisition device 240 at multiple locations therealong. In practice, this method of tissue acquisition may allow the operator some freedom to manipulate the acquired tissue by the relative movement of device inner distal portion 242 and the device outer distal portion 232. This technique can also assist in positioning the tissue to be fixed, and/or assuring that the required amount of tissue (e.g. some muscular layers of the organ wall), have been uniformly acquired prior to fixation.

Figure 10A:
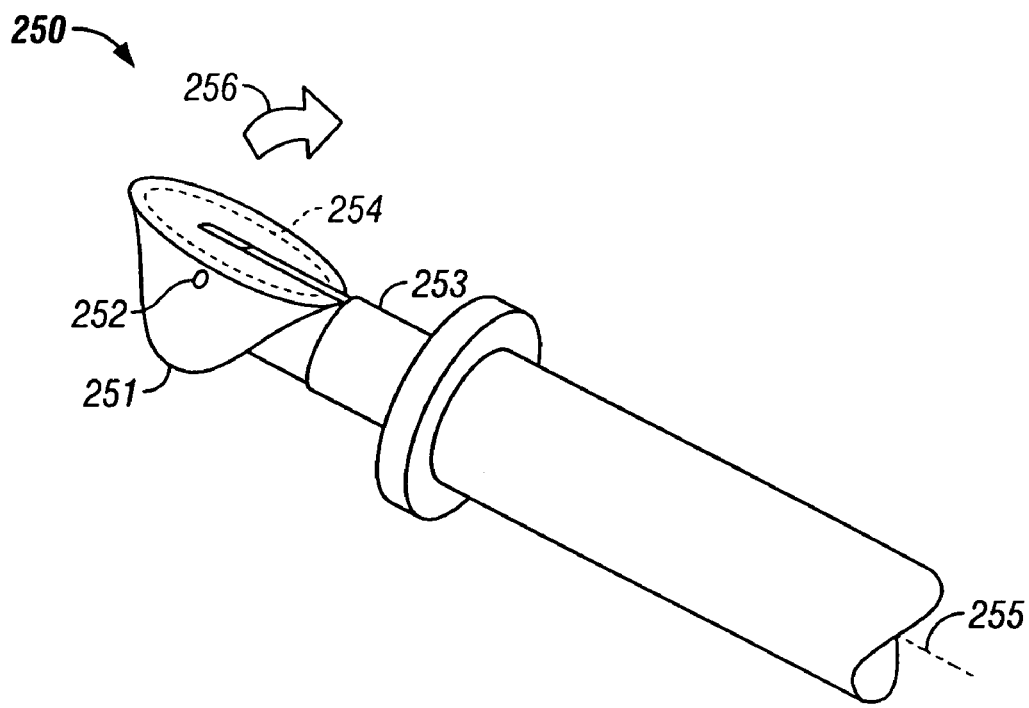
FIGS. 10A–10B depict variations of the distal working end of the distal tip of the circular tissue acquisition and fixation device of the present invention, detailing an anvil designed to be intraprocedurally manipulated to assist in removal of the circular tissue acquisition and fixation device of the present invention once the desired tissue has been acquired and fixed according to the present invention.
Figure 10B:
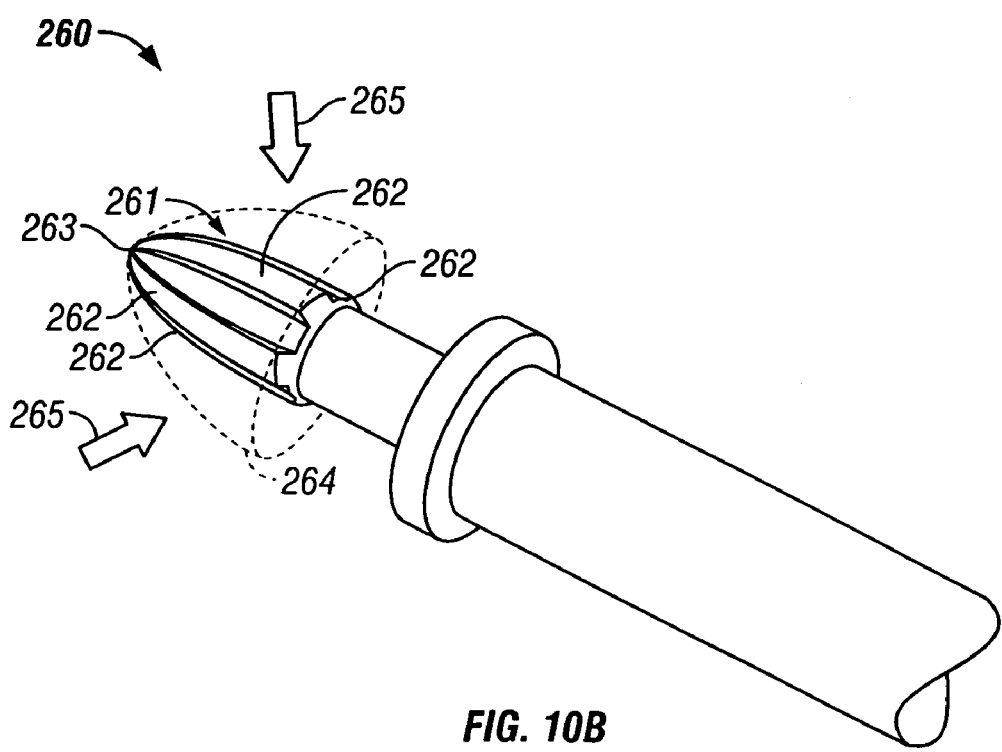

Following fixation, the tissue acquisition device of the present invention is withdrawn from the organ. In doing so, care should be used not to over-dilate or stretch the newly created tissue ring or stoma. To mitigate any dilation or stretching, the inner distal portion may also be modified. FIGS. 10A and 10B depict variations 250, 260 of the tissue acquisition inner distal portion that are adaptable to effectively reduce in cross sectional area to allow for easier removal of the tissue acquisition device from the organ once the circumferential fixation zone has been created. FIG. 10A depicts tissue acquisition device inner distal end 251 which is pivotally mounted on main body inner portion 253 about pin 252. Activation of the pivoting action may be controlled by release of an interface between pin 252 and a stay (not shown) housed within main body inner portion to activate rotation of inner distal end 251, e.g., in a direction 256. The inner distal end 251 may be rotated by any angle such the inner face 254 is angled or parallel relative to the longitudinal axis 255 of the device.

FIG. 10B depicts another variation 260 on tissue acquisition inner portion distal end which may have a segmented configuration. In this variation 260, the inner portion distal end may be made of a plurality of individual segments 262 which when collapsed, reduces the diameter of inner portion distal end to facilitate removal. Thus, during tissue acquisition and/or fixation, the expanded inner distal portion 264 may be utilized and after the procedure, it may then be compressed radially 265 about a pivot 263 to reduce the cross-sectional profile for removal from the area.

The steps of performing the method of organ division or reduction (transoral stomach reduction) are used to illustrate in detail the method and devices of the present invention, however the present invention is not limited thereby. Use of these steps and the tools deployed therein may be varied to achieve a similar result in other hollow body organs and it is anticipated that such techniques can be employed to divide or restrict other hollow body organs such as organs of the gastrointestinal tract such as bowel, stomach or intestine, or in procedures in the bladder (treatment for incontinence by reinforcing the bladder sphincter) or uterus, etc. In addition, as previously mentioned, other procedures such as the treatment of GERD may also benefit from the methods and devices disclosed herein. While certain embodiments have been illustrated and described in detail, those having ordinary skill in the art will appreciate that various alternatives, modifications, and equivalents may be used and that the invention is not intended to be limited to the specifics of these variations.

We claim:

1. A bypass conduit assembly for placement within a stomach, comprising:
   a device configured to form a narrowed region incorporating at least two layers of tissue created adjacent to or within the stomach;
   a flexible tubular member having a proximal end, a distal end, and a length therebetween with a lumen defined through the length;
   a fastener, extending through the proximal end of the tubular member thereby attaching the proximal end to the narrowed region incorporating at least two layers of tissue;
   the tubular member being configured to conform to the narrowed region incorporating at least two layers of tissue; and
   wherein the length of the tubular member extends from the narrowed region incorporating at least two layers of tissue so that the distal end is positioned distally of stomach such that the stomach is bypassed.

2. The bypass conduit of claim 1 wherein the tubular member is comprised of a biocompatible polymer.

3. The bypass conduit of claim 1 wherein the fastener is selected from the group consisting of clips, stents, and staples.

4. The bypass conduit of claim 1, further comprising a distal fastener, the distal end being affixed by the distal fastener to tissue located distally of the stomach.

5. The bypass conduit of claim 1 wherein the distal end is unanchored.

6. A bypass conduit assembly for placement within a stomach, comprising:
   a flexible tubular member having a proximal end, a distal end, and a length therebetween with a lumen defined through the length;
   a stent, attached to the proximal end of the tubular member and to a narrowed region of tissue created adjacent to or within the stomach, the stent being expandable to form an interference fit between the proximal end of the tubular member and the narrowed region of tissue; and
   wherein the length of the tubular member extends from the narrowed region of tissue so that the distal end is positioned distally of stomach such that the stomach is bypassed.

* * * * *